United States Patent [19]

Stanek et al.

[11] Patent Number: 5,461,076
[45] Date of Patent: Oct. 24, 1995

[54] HYDRAZONES

[76] Inventors: Jaroslav Stanek, Hangstrasse 9, 4144 Arlesheim; Jörg Frei, Buechring 36, 4434 Hölstein; Giorgio Caravatti, Baselmattweg 145/C, 4123 Allschwil, all of Switzerland

[21] Appl. No.: 346,964

[22] Filed: Nov. 30, 1994

Related U.S. Application Data

[62] Division of Ser. No. 218,854, Mar. 28, 1994, Pat. No. 5,395,855, which is a continuation of Ser. No. 939,782, Sep. 3, 1992, abandoned, which is a continuation-in-part of Ser. No. 695,858, May 6, 1991, abandoned.

[30] Foreign Application Priority Data

May 7, 1990 [CH] Switzerland ............................. 1538/90
Oct. 16, 1991 [CH] Switzerland ............................. 3041/91

[51] Int. Cl.$^6$ ................ A61K 31/15; A61K 31/155; C07C 281/16
[52] U.S. Cl. ............ 514/632; 514/582; 514/590; 514/601; 514/602; 514/603; 514/631; 514/639; 564/19; 564/36; 564/80; 564/81; 564/225; 564/226; 564/227; 564/228
[58] Field of Search .................. 514/582, 590, 514/631, 632, 639, 601, 602, 603; 564/19, 36, 225, 226, 227, 228, 80, 81

[56] References Cited

U.S. PATENT DOCUMENTS

| | | | |
|---|---|---|---|
| 3,956,363 | 5/1976 | Shen et al. ............... | 560/108 |
| 4,076,726 | 2/1978 | Pannemann et al. ........ | 560/139 |
| 4,080,449 | 5/1978 | Crosier et al. ........... | 514/213 |
| 4,971,986 | 11/9199 | Stanek et al. ............ | 514/357 |

FOREIGN PATENT DOCUMENTS

| | | |
|---|---|---|
| 377304 | 7/1990 | European Pat. Off. . |
| 0894693 | 10/1953 | Germany . |
| 2733868 | 2/1978 | Germany . |
| 3416695 | 11/1985 | Germany . |
| 9103391 | 12/1991 | South Africa . |
| 9107382 | 5/1991 | WIPO . |

OTHER PUBLICATIONS

Chem Abst 104:207159v (1986) Corresponding to "AM" above.
Chem Abst 109:92791d (1988) Corresponding to CN 85 101 799 Jan. 17, 1987.
Chem Abst 1958, 14678a Corresponding to AP Above Jensch, DE 894693.
Chem Abst 105:6283c (1986). Gan et al. "Synthesis of Indanones and Tetralones as new potential Schistosomicidals," Yaoxue Xuebao 1985, 20(5) 342–52.
Misra et al, J. Indian Chem. Soc. vol. 52, Oct. 1975, pp. 981–982 "Synthesis and Antibacterial Activity of Thiosemicarbazones and Hydrazones Derived from Indanone–1".
Chem Abst 107:77634v (1987) Corresponding to WO 86 04582 Aug. 14, 1986 and U.S. application Ser. No. 700,375, filed Feb. 11, 1985.
Sam et al, J. Pharmacol. Sci. 53, 1364–1368 (1965) "Potential Antineoplastic Agents Derived from 1,2-Epoxylindan."
Chatterjea et al., J. Indian Chem Soc. 37, No. 8, 1960, pp. 443–450, "The Course of Cyclization of β–Benzylhomophthalic Acids."
Juhani Jänne et al, Biochem J. (1984) 218, 947–951 "Inhibition of S–adenosylmethionine decarboxylase and diamine oxidase activities by analogues of methylglyoxal bis(guanylhydrazone) and their cellular uptake during lymphocyte activation".
Patai (ed); "The Chemistry of Amidines and Imidates." Wiley & Sons, London 1975 pp. 303–304.
Williams–Ashman et al; Biochem. Biophys. Res. Commun. 46,288 (1972) "Methyl Glyoxal Bis(guanylhydrazone) as a Potent Inhibitor of Mammalian and Yeast S–adenosylmethionine Decarboxylases."
Dondoni; J. Chem. Soc. Chem. Commun. 1975, 761–762, "Synthetic Reactions using Transition Metal Complexes. Conversion of Amide Oximes into Amidines by Pentacarbonyliron and Evidence for Imine Intermediates in the Deoximation of Ketoximes".
Adamczyk et al; J. Org. Chem. 1984, 49 pp. 4226–4327 "Synthesis of Biological Markers in Fossil Fuels 2. Synthesis and $^{13}$C NMR Studies of Substituted Indans and Tetralins."
Miyake et al; Chem. Pharm. Bull. 31, (7), 2329–2348 (1983) "Synthesis of 2–(N–Substituted amino)–6–hydroxy–1,2,3, 4–tetrahydronaphthalen–1–ol Derivatives".
Munavalli et al; Bull. Soc. Chim. France 1964 (12) pp. 3103–3112. "Synth`ese de dérivés indaniques." & corresponding Chem Abstr. 62:7702e–7703h.
Jackson et al; J. Chem. Soc. Perkin Trans. 1974, pp. 1911–1920. "Phenol Oxidation. Part III. Synthesis of the Benzylisoquinoline Alkaloid Cularine."
Bartmann et al; J. Heterocyclic Chem. 24, 677–682, 1987 "Synthesis of Di– and Tetraalkyl–3–piperazinoisoquinolines and Related Compounds as Potential Antidepressant Agents."
Sakar et al; Indian J. Chem., vol. 24B, Oct. 1985, pp. 1061–1064 "One–Step Preparation of Some Synthetically Useful Indanones."
Klein et al; J. Org. Chem., vol. 22, 1019–1021, Sep. 1957 "Synthesis of 8–Bromo–1–Methylnaphthalene from o–Bromoacetophenone."

*Primary Examiner*—Shailendra Kumar
*Attorney, Agent, or Firm*—Irving M. Fishman; Karen G. Kaiser

[57] ABSTRACT

Compounds of formula I

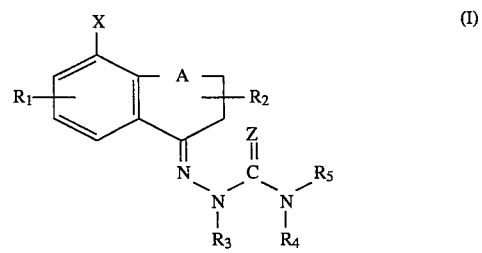

wherein A, X, Z and $R_1$–$R_5$ are as defined in the description, and their salts have valuable pharmaceutical properties and are effective especially against tumors. They are prepared in a manner known per se.

6 Claims, No Drawings

HYDRAZONES

This is a DIVISIONAL of Ser. No. 218,854, now U.S. Pat. No. 5,395,855, filed Mar. 28, 1994, which is a CONTINUATION of Ser. No. 939,782, filed Sep. 3, 1992, now abandoned, which is a CONTINUATION IN PART of Ser. No. 695,858, filed May 6, 1991, now abandoned.

The invention relates to compounds of formula I

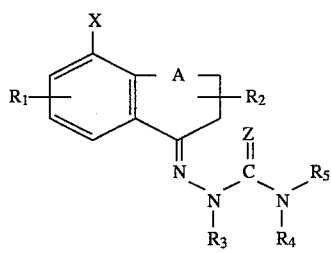

wherein A is a direct bond or —$(CH_2)_n$—, wherein n is 1, 2 or 3; X is a radical —C(=Y)—$NR_6R_7$; Y is $NR_8$, O or S; Z is $NR_9$, O or S; $R_1$ and $R_2$ are each independently of the other hydrogen or one or more substituents other than hydrogen; the radicals $R_3$, $R_4$, $R_6$, $R_8$ and $R_9$ are each independently of the others hydrogen or lower alkyl; and $R_5$ and $R_7$ are each independently of the other hydrogen, lower alkyl, hydroxy, etherified or esterified hydroxy or unsubstituted or mono- or di-substituted amino; tautomers thereof, and salts thereof, especially certain acid addition salts, to a process for the preparation of those compounds, to pharmaceutical compositions comprising those compounds, to the use of those compounds for the therapeutic treatment of the human or animal body or for the manufacture of pharmaceutical compositions.

Tautomers may occur, for example, when Z is $NR_9$ and $R_3$ and/or $R_4$ and/or $R_5$ are hydrogen:

The corresponding guanyl radical, represented by —$N(R_3)$—C(=Z)—$NR_4R_5$ in formula I, can then, for example, also be in the tautomeric form —N=C(—ZH)—$NR_4R_5$, —$N(R_3)$—C(—ZH)=$NR_5$ or —$N(R_3)$—C(—ZH)=$NR_4$.

A further example: when Y is $NR_8$ and $R_6$ and/or $R_7$ is hydrogen, then the corresponding amidine structure, defined as X=—C(=Y)—$NR_6R_7$ in formula I, may also be in the tautomeric form —C(—YH)=$NR_7$ or —C(—YH)=$NR_6$. The existence of those and similar tautomers is familiar to the person skilled in the art. All those tautomers are covered by the general formula I.

In the case where A is a group —$(CH_2)_n$— and $R_2$ is other than hydrogen, the substituent(s) corresponding to the radical $R_2$ can also be linked to the carbon atoms of the group —$(CH_2)_n$—.

$R_2$ is, for example, hydrogen or from one to four substituents other than hydrogen, especially hydrogen or one or two substituents other than hydrogen and more especially hydrogen or one substituent other than hydrogen.

$R_1$ is, for example, hydrogen or from one to three substituents other than hydrogen and especially hydrogen or one or two substituents other than hydrogen.

The general terms used hereinabove and hereinbelow preferably have the following meanings in the context of this Application:

The term "lower" denotes a radical having up to and including 7 and especially up to and including 4 carbon atoms.

Lower alkyl is, for example, n-propyl, isopropyl, n-butyl, isobutyl, sec-butyl, tert-butyl, n-pentyl, neopentyl, n-hexyl or n-heptyl, preferably ethyl and especially methyl.

A substituent other than hydrogen is, for example, lower alkyl, triflouromethyl, cycloalkyl, aryl-lower alkyl, hydroxy, lower alkoxy, aryl-lower alkoxy, aryloxy; acyloxy, for example lower alkanoyloxy; halogen, amino, N-lower alkylamino, N,N-di-lower alkylamino; acylamino, for example lower alkanoylamino; nitro, lower alkanoyl, arylcarbonyl, carboxy, lower alkoxycarbonyl, carbamoyl (—$CONH_2$), N-lower alkylcarbamoyl, N,N-di-lower alkylcarbamoyl, N-arylcarbamoyl, cyano, mercapto, lower alkylthio, lower alkylsulfonyl, sulfamoyl (—$SO_2NH_2$), N-lower alkylsulfamoyl or N,N-di-lower alkylsulfamoyl.

Aryl is, for example, phenyl or naphthyl, such as 1- or 2-naphthyl. The phenyl and naphthyl radicals can be unsubstituted or substituted, especially as indicated below for phenyl. Aryl is preferably phenyl that is unsubstituted or substituted by one or more, especially one or two, substituents from the group consisting of lower alkyl, lower alkoxy, hydroxy, lower alkanoyloxy, nitro, amino, halogen, trifluoromethyl, carboxy, lower alkoxycarbonyl, carbamoyl, N-lower alkylcarbamoyl, N,N-di-lower alkylcarbamoyl, cyano, lower alkanoyl, arylcarbonyl, lower alkylsulfonyl, sulfamoyl, N-lower alkylsulfamoyl and N,N-di-lower alkylsulfamoyl. Aryl is especially phenyl that is unsubstituted or substituted by lower alkyl, lower alkoxy, hydroxy, halogen or by trifluoromethyl, and is more especially phenyl.

Arylcarbonyl is, for example, benzoyl that is unsubstituted or substituted by lower alkyl, lower alkoxy, hydroxy, halogen or by trifluoromethyl, and is especially benzoyl.

Aryl-lower alkyl is, for example, phenyl-lower alkyl and especially benzyl.

Halogen is especially chlorine and bromine, but may also be fluorine or iodine.

Lower alkanoyl is, for example, formyl, acetyl, propionyl or pivaloyl.

Cycloalkyl is preferably $C_3$–$C_8$- and especially $C_5$–$C_6$cycloalkyl, which is intended to indicate that it contains from 3 to 8 and 5 or 6 ring carbon atoms, respectively. It may, however, also be substituted, for example by lower alkyl.

Etherified hydroxy is, for example, lower alkoxy. Esterified hydroxy is, for example, lower alkanoyloxy. Monosubstituted amino is, for example, lower alkylamino. Di-substituted amino is, for example, di-lower alkylamino, lower alkyleneamino, for example $C_4$–$C_7$- and especially $C_4$–$C_5$-alkyleneamino, for example piperidino, or oxa-, thia- or aza-lower alkyleneamino, for example morpholino, thiomorpholino, piperazino or 4-lower alkylpiperazino.

Salts of compounds according to the invention are especially pharmaceutically acceptable, non-toxic salts. For example, compounds of formula I having basic groups may form acid addition salts, for example with inorganic acids, such as hydrochloric acid, sulfuric acid or phosphoric acid, or with suitable organic carboxylic or sulfonic acids, for example acetic acid, fumaric acid or methanesulfonic acid, or, for example, with amino acids, such as arginine or lysine. When several basic groups are present, mono- or poly-salts may be formed. Compounds of formula I having an acidic group, for example carboxy, and a basic group, for example amino, may be, for example, in the form of internal salts, that is to say in zwitterionic form, or part of the molecule may be in the form of an internal salt and another part may be in the form of a normal salt.

The aim of the present invention is also to provide novel acid addition salts of pharmacologically acceptable compounds, which salts have a good solubility in physiological liquids and/or liquids that are similar to physiological liquids, such as physiological saline solution, mannitol solution or phosphate buffers, and/or good absorbability in the case of enteral, such as oral, administration, for example by the formation of ion pairs, such as lipophilic ion pairs.

The acid addition salts according to the invention of bases of formula I are comprising those with an acid [PA] that is a mono-or poly-protic acid selected from carbonic acid, alkanoic acids that are unsubstituted or mono- or poly-substituted, with the exception of formic acid, unsubstituted acetic acid, lysine and arginine; alkenoic acids that are unsubstituted or substituted, with the exception of unsubstituted fumaric acid; cycloalkylcarboxylic acids, arylcarboxylic acids, aryl-lower alkylcarboxylic acids, wherein lower alkyl is unsubstituted or substituted, aryl-lower alkenylcarboxylic acids, heterocyclylcarboxylic acids, alkanesulfonic acids that are unsubstituted or substituted, with the exception of unsubstituted methanesulfonic acid; aromatic sulfonic acids, alkylsulfuric acids, N-substituted sulfamic acids, organic acids without carboxy, sulfo, sulfate or phospho groups, and also selected from pyrophosphoric acid and hydriodic acid, and tautomers thereof.

The invention also relates to to processes for the preparation of those acid addition salts, to pharmaceutical compositions comprising those acid addition salts, and to the use of those acid addition salts in the therapeutic treatment of the human or animal body or in the preparation of pharmaceutical compositions.

The following definitions relate to the acids [PA] ([PA] stands for "Protic Acid"):

Alkanoic acids are especially $C_1$–$C_{20}$alkanoic acids with the exception of formic acid and unsubstituted acetic acid, preferably $C_2$–$C_7$alkanoic acids, such as propionic acid, butyric acid, isobutyric acid, pentanoic acid, hexanoic acid or heptanoic acid, or also octanoic acid, decanoic acid or dodecanoic acid, especially propionic acid or octanoic acid, all of those alkanoic acids being unsubstituted or substituted one or more times, especially from one to six times, preferably by hydroxy, either once, such as in glycolic acid, lactic acid or 2-hydroxybutyric acid, or several times, for example up to five times, such as in gluconic acid or glucose monocarboxylic acid ("glucoheptonic acid"), by carboxy, for example in $C_2$–$C_{20}$alkanoic di-acids, especially $C_2$–$C_7$alkanoic di-acids, such as in succinic acid, or also adipic acid, pimelic acid, suberic acid or azelaic acid, by hydroxy and carboxy, such as in malic acid, tartaric acid, citric acid, glucaric acid or galactaxic acid, by amino or amino and carboxy and/or by one or two radicals selected independently from mercapto, methylmercapto, hydroxy, phenyl, 4-hydroxyphenyl, naphthyl, cyclohexyl, imidazolyl and indolyl, such as in amino acids, lysine and arginine being excluded, especially glutamic acid or aspartic acid in the (D)-, (L)- or (D,L)-form, preferably the (D)- or (L)-form, by substituted amino or substituted amino and carboxy and/or by one or two radicals selected independently from mercapto (also in oxidised form as the corresponding disulfide consisting of two molecules of the corresponding mercaptan), methylmercapto, hydroxy, phenyl, 4-hydroxyphenyl, naphthyl, cyclohexyl, imidazolyl and indolyl, such as in amino acids, for example in N-mono- or N,N-di-lower alkylamino acids, such as N-methylglycine, or in N-lower alkanoylamino acids, such as acetylaminoacetic acid (N-acetylglycine), N-acetylasparagine or N-acetylcystine, by oxo, such as in pyruvic acid or acetoacetic acid, by phospho and amino, such as in phosphoserine, or by phospho and hydroxy, such as in 2- or 3-glycerophosphoric acid, glucose-6-phosphoric acid, glucose-1-phosphoric acid or fructose-1,6-bisphosphoric acid. Amino acids are especially α-amino acids which may be in the (D)-, (L)- or (D,L)-form, preferably the (L)- or (D)-form, and, when other centers of asymmetry are present, they may also be in the form of other isomers, for example selected from glycine (H-Gly-OH), alanine (H-Ala-OH), valine (H-Val-OH), norvaline (α-aminovaleric acid), leucine (H-Leu-OH), isoleucine (H-Ile-OH), norleucine (α-aminohexanoic acid, H-Nle-OH), serine (H-Ser-OH), homoserine (α-amino-γ-hydroxybutyric acid), threonine (H-Thr-OH), methionine (H-Met-OH), cysteine (H-Cys-OH) (which may also be present in oxidised form as cystine), phenylalanine (H-Phe-OH), tyrosine (H-Tyr-OH), β-phenylserine (β-hydroxyphenylalanine), phenylglycine, α-naphthylalanine (H-Nal-OH), cyclohexylalanine (H-Cha-OH), cyclohexylglycine, tryptophan (H-Trp-OH), aspartic acid (H-Asp-OH), asparagine (H-Asn-OH), aminomalonic acid, glutamic acid (H-Glu-OH), glutamine (H-Gln-OH), histidine (H-HisOH), δ-hydroxylysine, ornithine (α,δ-diaminovaleric acid), α,δ-diaminobutyric acid and α,β-diaminopropionic acid, and, unless otherwise indicated, from arginine (H-Arg-OH) and lysine (H-Lys-OH). Especially preferred amino acids are glycine, serine, cystine, aspartic acid and glutamic acid, especially aspartic acid and glutamic acid. Amino acids may also be omitted from the definition of substituted alkanoic acids.

Alkenoic acids are, for example, $C_2$–$C_{10}$alkenoic di-acids that are unsubstituted, such as maleic acid, or substituted, preferably by hydroxy, such as in hydroxymaleic acid (tautomer: oxalacetic acid), or lower alkyl, for example methyl, such as in methylmaleic acid. Unsubstituted fumaric acid is excluded.

Cycloalkylcarboxylic acids are preferably $C_4$–$C_{12}$cycloalkylcarboxylic acids wherein the cycloalkyl radical is mono-, bi- or tri-cyclic, preferably monocyclic or tricyclic, for example cyclopentyl, cyclohexyl, cycloheptyl or adamantyl, and is, for example, unsubstituted, such as in cyclohexanecarboxylic acid or adamantanecarboxylic acid.

In arylcarboxylic acids, the aryl radical has, for example, from 6 to 20, preferably from 6 to 14, carbon atoms, and is selected, for example, from phenyl, 1- or 2-naphthyl and indane, and is unsubstituted, such as in benzoic acid, or substituted, preferably by from 1 to 3 radicals selected independently from lower alkyl, such as methyl, halogen, such as fluorine, chlorine or bromine, hydroxy, lower alkoxy, for example methoxy, phenoxy, lower alkanoyloxy, such as acetoxy, amino and carboxy, such as in salicylic acid, 1- or 3 -hydroxynaphthyl-2-carboxylic acid, 3,4,5-trimethoxybenzoic acid, 2-phenoxybenzoic acid, 2-acetoxybenzoic acid, 4-aminosalicylic acid or phthalic acid.

In aryl-lower alkylcarboxylic acids, aryl is as last defined for arylcarboxylic acids and is unsubstituted or substituted as defined there, and lower alkyl is preferably methyl or ethyl, lower alkyl being unsubstituted, such as in phenylacetic acid, or substituted, for example by hydroxy, such as in mandelic acid.

In aryl-lower alkenylcarboxylic acids, aryl is as last defined for arylcarboxylic acids, and lower alkenyl has preferably from 2 to 4 carbon atoms, such as in cinnamic acid.

Heterocyclylcarboxylic acids contain, for example, heterocyclyl comprising from one to three rings, preferably one or two rings, that is saturated or partially or completely unsaturated, preferably saturated or unsaturated, and has from 5 to 12 ring atoms, preferably from 5 to 7 ring atoms, which are selected from carbon and up to three hetero atoms, preferably one or two hetero atoms being present, especially oxygen, nitrogen and/or sulfur, especially oxygen and nitrogen, heterocyclyl being, for example, pyrrolyl, imidazolyl, pyrazolyl, oxazolyl, pyrazinyl, pyrimidinyl, indolyl, quinolyl, isoquinolyl, quinoxalinyl or a completely or partially saturated derivative of those radicals, or pyranyl or furanyl, and being unsubstituted, such as in nicotinic acid or isonicotinic acid, or from mono- to penta-substituted, preferably by hydroxy and/or by hydroxy-lower alkyl, for example hydroxy or hydroxymethyl, such as in glucuronic acid or galacturonic acid.

Alkanesulfonic acids are especially $C_2$–$C_{20}$alkanesulfonic acids, preferably $C_2$–$C_7$alkylsulfonic acids, such as ethanesulfonic acid, that are unsubstituted or substituted, preferably by one or two radicals selected from hydroxy and sulfo, such as in 2-hydroxyethanesulfonic acid, or alkanedisulfonic acids, for example lower alkanedisulfonic acids, such as ethane-1,2-disulfonic acid. Methanesulfonic acid is excluded.

In aromatic sulfonic acids, the aromatic residue is, for example, aryl as defined for arylcarboxylic acids and is unsubstituted, such as in benzenesulfonic acid or 2-naphthalenesulfonic acid, or is substituted as in arylcarboxylic acids, especially by lower alkyl, for example methyl, such as in 2-, 3- or 4-methylbenzenesulfonic acid, or by a further sulfonyl radical, such as in 1,3-benzenesulfonic acid or naphthalene-1,5-disulfonic acid, such as, especially, in 1,5-naphthalenedisulfonic acid.

Alkylsulfuric acids are especially $C_1$–$C_{20}$alkylsulfuric acids, especially lower alkylsulfuric acids, such as methylsulfuric acid or ethylsulfuric acid, or dodecylsulfuric acid.

N-substituted sulfamic acids are, for example, N-cycloalkylsulfamic acids, wherein cycloalkyl is preferably $C_4$–$C_{12}$cycloalkyl and the cycloalkyl radical is mono-, bi- or tri-cyclic, for example cyclopentyl, cyclohexyl, cycloheptyl or adamantyl, preferably monocyclic, such as in N-cyclohexylsulfamic acid, or N-alkylsulfamic acids, preferably N-lower alkylsulfamic acid, such as methyl-, ethyl- or propyl-sulfamic acid.

Organic acids without carboxy, sulfo, sulfate or phospho groups contain, for example, acidic hydroxy groups, such as in ascorbic acid.

Important acids are carbonic acid, propionic acid, octanoic acid, decanoic acid, dodecanoic acid, glycolic acid, lactic acid, 2-hydroxybutyric acid, gluconic acid, glucose monocarboxylic acid, succinic acid, adipic acid, pimelic acid, suberic acid, azelaic acid, malic acid, tartaric acid, citric acid, glucaric acid, galactaric acid, glutamic acid, aspartic acid, N-methylglycine, acetylaminoacetic acid, N-acetylasparagine, N-acetylcystine, pyruvic acid, acetoacetic acid, phosphoserine, 2- or 3-glycerophosphoric acid, glucose-6-phosphoric acid, glucose-1-phosphoric acid, fructose-1,6-bisphosphoric acid, maleic acid, hydroxymaleic acid, methylmaleic acid, cyclohexanecarboxylic acid, adamantanecarboxylic acid, benzoic acid, salicylic acid, 1- or 3-hydroxynaphthyl-2-carboxylic acid, 3,4,5-trimethoxybenzoic acid, 2-phenoxybenzoic acid, 2-acetoxybenzoic acid, 4-aminosalicylic acid, phthalic acid, phenylacetic acid, mandelic acid, cinnamic acid, nicotinic acid, isonicotinic acid, glucuronic acid, galacturonic acid, ethanesulfonic acid, 2-hydroxyethanesulfonic acid, ethane-1,2-disulfonic acid, benzenesulfonic acid, 2-naphthalenesulfonic acid, 1,5-naphthalenedisulfonic acid, 2-, 3- or 4-methylbenzenesulfonic acid, methylsulfuric acid, ethylsulfuric acid, dodecylsulfuric acid, N-cyclohexylsulfamic acid, methyl-, ethyl- or propyl-sulfamic acid, or ascorbic acid.

Very important acids are octanoic acid, succinic acid, adipic acid, salicylic acid, benzenesulfonic acid, 1,5-naphthalenesulfonic acid or N-cyclohexylsulfamic acid, very especially salicylic acid or, more especially, adipic acid or benzenesulfonic acid.

Very important acids are equally tartaric acid, especially L-tartaric acid, lactic acid or citric acid.

The mentioned acids, especially if they contain several acidic groups of differing acidity that can dissociate protons, may also be in the form of mixed salts with cations, for example alkali metal cations, such as sodium or potassium ions, alkali metal salts, such as magnesium salts, or zinc salts, the acid component before the reaction yielding the mentioned mixed salts containing at least one other dissociable proton, or they may be present in the resulting salts in a form in which not all protons are freed, but at least one proton has been transferred to the relevant base of formula I. For example, carbonic acid can be used in the form of a hydrogen carbonate salt, such as sodium or potassium hydrogen carbonate.

The acid addition salts of a base of formula I with an acid [PA] may also be in the form of hydrates. Crystals may also include other solvents used for crystallization.

For the purposes of isolation or purification it is also possible to use pharmaceutically unacceptable salts, for example picrates or perchlorates. Only the pharmaceutically acceptable, non-toxic salts are used therapeutically and these are therefore preferred. Depending on the structural configuration, the compounds of formula I and their salts, especially their acid addition salts, for example, with acids [PA], of the present invention may be in the form of isomeric mixtures or in the form of pure isomers. If, for example, $R_2$ is a substituent other than hydrogen, the corresponding compound of formula I or the acid addition salts of compounds of formula I may be in the form of racemates or racemic salts or of enantiomers or enantiomerically pure salts or, especially in the case of a salt with an acid [PA], also in the form of diastereoisomeric salts, for example in the presence of acids having centers of asymmetry, such as the mentioned amino acids, lactic acid or tartaric acid.

The compounds according to the invention, especially their acid addition salts, have valuable, especially pharmacologically acceptable, properties. In particular, they have a strong, specific inhibitory action on the enzyme S-adenosylmethionine decarboxylase (SAMDC). SAMDC as a key enzyme plays an important part in the polyamine synthesis that takes place in virtually all cells of mammals, including humans. The polyamine concentration in the cell is regulated by SAMDC. Inhibition of the SAMDC enzyme results in a reduction in the polyamine concentration. Since a reduction in the polyamine concentration effects inhibition of cell growth, it is possible by administering SAMDC-inhibiting substances to inhibit the growth of both eukaryotic and prokaryotic cells and even to kill cells or to inhibit the onset of cell differentiation.

The inhibition of the SAMDC enzyme can be demonstrated, for example, using the method of H. G. Williams-Ashmann and A. Schenone, Biochem. Biophys. Res. Communs. 46, 288 (1972). The compounds of the invention have $IC_{50}$ values of a minimum of approximately 0.005 μM.

A further advantage of the compounds according to the invention lies in the fact that in comparison with their strong inhibitory action on SAMDC their inhibitory action on diamine oxidase is only slight and they are well tolerated. According to J. Jaenne and D. R. Morris, Biochem. J. 218,974 (1984), the inhibition of diamine oxidase is disadvantageous since it can result in an accumulation of putrescine and indirect SAMDC activation.

The compounds of formula I are therefore, for example, useful for the treatment of benign and malignant tumours. They can bring about the recession of tumours and also prevent the spread of tumour cells and the growth of micrometastases. Furthermore, they can be used, for example, for the treatment of protozoa infections, for example trypanosomiasis, malaria, or pulmonary inflammation caused by *Pneumocystis carinii*.

As selective SAMDC-inhibitors, the compounds of formula I, or especially their acid addition salts, can be used alone or alternatively in combination with other pharmacologically active substances. Possible combinations are, for example, a combination with (a) inhibitors of other enzymes of the polyamine biosynthesis, for example ornithine decarboxylase inhibitors, (b) inhibitors of protein kinase C, (c) inhibitors of tyrosine protein kinase, (d) cytokines, (e) negative growth regulators, (f) aromatase inhibitors, (g) anti-oestrogens or (h) classic cytostatic active ingredients.

The invention relates preferably to compounds of formula I wherein A is a direct bond or —$(CH_2)_n$—, wherein n is 1 or 2; X is a radical —$C(=Y)$—$NR_6R_7$; Y is $NR_8$, O or S; Z is $NR_9$, O or S; $R_1$ and $R_2$ are each independently of the other hydrogen or one or two substituents from the group consisting of lower alkyl, trifluoromethyl, cycloalkyl, aryl-lower alkyl, hydroxy, lower alkoxy, aryl-lower alkoxy, aryloxy, lower alkanoyloxy, halogen, amino, N-lower alkylamino, N,N-di-lower alkylamino, lower alkanoylamino, nitro, lower alkanoyl, arylcarbonyl, carboxy, lower alkoxycarbonyl, carbamoyl, N-lower alkylcarbamoyl, N,N-di-lower alkylcarbamoyl, N-arylcarbamoyl, cyano, mercapto, lower alkylthio, lower alkylsulfonyl, sulfamoyl, N-lower alkylsulfamoyl and N,N-di-lower alkylsulfamoyl, aryl being phenyl that is unsubstituted or substituted by lower alkyl, lower alkoxy, hydroxy, halogen or by trifluoromethyl; the radicals $R_3$, $R_4$, $R_6$, $R_8$ and $R_9$ are each independently of the others hydrogen or lower alkyl; and $R_5$ and $R_7$ are each independently of the other hydrogen, lower alkyl, hydroxy, lower alkoxy, lower alkanoyloxy, amino, lower alkylamino, di-lower alkylamino, lower alkyleneamino or oxa-, thia- or aza-lower alkyleneamino; tautomers thereof, and salts thereof.

Preference is given especially to compounds of formula I wherein A is a direct bond or —$(CH_2)_n$—, wherein n is 1 or 2; X is a radical —$C(=Y)$—$NR_6R_7$; Y is NH, O or S; Z is NH, O or S; $R_1$ and $R_2$ are each independently of the other hydrogen or one or two substituents from the group consisting of lower alkyl, trifluoromethyl, phenyl-lower alkyl, hydroxy, lower alkoxy and halogen; the radicals $R_3$, $R_4$ and $R_6$ are hydrogen; and $R_5$ and $R_7$ are each independently of the other hydrogen, lower alkyl, hydroxy or amino; tautomers thereof, and salts thereof.

Preference is given more especially to compounds of formula I wherein A is a direct bond or —$CH_2$—; X is a radical —$C(=Y)$—$NR_6R_7$; Y is NH or S; Z is NH; $R_1$ is hydrogen or one or two substituents from the group consisting of lower alkyl, hydroxy, lower alkoxy and halogen; $R_2$ is hydrogen or lower alkyl; the radicals $R_3$, $R_4$ and $R_6$ are hydrogen; and $R_5$ and $R_7$ are each independently of the other hydrogen, lower alkyl or hydroxy; tautomers thereof, and pharmaceutically acceptable salts thereof.

Very special preference is given to compounds of formula I wherein A is a direct bond, X is a radical —$C(=NH)$—$NH_2$; Z is NH; $R_1$ is hydrogen or one or two substituents from the group consisting of lower alkyl, hydroxy and lower alkoxy; the radicals $R_2$, $R_3$ and $R_4$ are hydrogen; and $R_5$ is hydrogen or hydroxy; tautomers thereof, and pharmaceutically acceptable salts thereof.

Special mention should be made of each of the following sub-groups of a group of compounds of formula I:

(a) compounds of formula I wherein A is a direct bond; (b) compounds of formula I wherein X is a radical —$C(=NH)$—$NH_2$; (c) compounds of formula I wherein Z is NH, $R_4$ is hydrogen and $R_5$ is hydrogen or hydroxy; and (d) compounds of formula I wherein $R_1$ and $R_2$ are hydrogen.

The invention relates especially to the specific compounds described in the Examples and salts thereof.

With special regard to the acid addition salts of bases of formula I, the invention relates preferably to the acid addition salts of a base of formula I wherein A is a direct bond or —$(CH_2)_n$—, n being 1 or 2; X is a radical —$C(=Y)$—$NR_6R_7$; Y is $NR_8$, O or S; Z is $NR_9$, O or S; each of $R_1$ and $R_2$, independently of the other, is hydrogen or one or two substituents selected from the group consisting of lower alkyl, trifluoromethyl, cycloalkyl, aryl-lower alkyl, hydroxy, lower alkoxy, aryl-lower alkoxy, aryloxy, lower alkanoyloxy, halogen, amino, N-lower alkylamino, N,N-di-lower alkylamino, lower alkanoylamino, nitro, lower alkanoyl, arylcarbonyl, carboxy, lower alkoxycarbonyl, carbamoyl, N-lower alkylcarbamoyl, N,N-di-lower alkylcarbamoyl, N-arylcarbamoyl, cyano, mercapto, lower alkylthio, lower alkylsulfonyl, sulfamoyl, N-lower alkylsulfamoyl and N,N-di-lower alkylsulfamoyl, aryl being phenyl that is unsubstituted or substituted by lower alkyl, lower alkoxy, hydroxy, halogen or by trifluoromethyl; each of the radicals $R_3$, $R_4$, $R_6$, $R_8$ and $R_9$, independently of the others, is hydrogen or lower alkyl; and each of $R_5$ and $R_7$, independently of the other, is hydrogen, lower alkyl, hydroxy, lower alkoxy, lower alkanoyloxy, amino, lower alkylamino, di-lower alkylamino, lower alkyleneamino or oxa-, thia- or aza-lower alkyleneamino;

with an acid [PA] that is a mono- or poly-protic acid selected from carbonic acid, alkanoic acids that are unsubstituted or mono- or poly-substituted, with the exception of formic acid, unsubstituted acetic acid, lysine and arginine; alkenoic acids that are unsubstituted or substituted, with the exception of fumaric acid; cycloalkylcarboxylic acids, arylcarboxylic acids, aryl-lower alkylcarboxylic acids, wherein lower alkyl is unsubstituted or substituted, aryl-lower alkenylcarboxylic acids, heterocyclylcarboxylic acids, alkanesulfonic acids that are unsubstituted or substituted, with the exception of methanesulfonic acid; arylsulfonic acids, alkylsulfuric acids, N-substituted sulfamic acids, organic acids without carboxy, sulfo, sulfate or phospho groups, and also selected from pyrophosphoric acid and hydriodic acid, for example one of the acids defined above as being important, for example one of the acids defined as being very important, or tautomers thereof.

Especially preferred are the acid addition salts of a base of formula I wherein A is a direct bond or —$(CH_2)_n$—, wherein n is 1 or 2; X is a radical —$C(=Y)$—$NR_6R_7$; Y is NH, O or S; Z is NH, O or S; each of $R_1$ and $R_2$, independently of the other, is hydrogen or one or two substituents selected from the group consisting of lower alkyl, trifluoromethyl, phenyl-lower alkyl, hydroxy, lower alkoxy and halogen; the radicals $R_3$, $R_4$ and $R_6$ are hydrogen; and each of $R_5$ and $R_7$, independently of the other, is hydrogen, lower alkyl, hydroxy or amino; with an acid [PA] that is a mono- or poly-protic acid selected from carbonic acid, alkanoic acids that are unsubstituted or mono- or poly-substituted, with the exception of formic acid, unsubstituted acetic acid, lysine and arginine; alkenoic acids that are unsubstituted or substituted, with the exception of fumaric acid; cycloalkylcarboxylic acids, arylcarboxylic acids, aryl-lower alkylcarboxylic acids, wherein lower alkyl is unsubstituted or substituted, aryl-lower alkenylcarboxylic acids, heterocyclylcarboxylic acids, alkanesulfonic acids that are unsubstituted or substituted, with the exception of methanesulfonic acid; aromatic sulfonic acids, alkylsulfuric acids, N-substituted sulfamic acids, organic acids without carboxy, sulfo, sulfate or phospho groups, and also selected from pyrophosphoric acid and hydriodic acid, for example one of the acids defined above as being important, for example one of the acids defined as being vry important;

or tautomers thereof.

More especially preferred are the acid addition salts of a base of formula I wherein A is a direct bond or —$CH_2$—; X is a radical —C(=Y)—$NR_6R_7$; Y is NH or S; Z is NH; $R_1$ is hydrogen or one or two substituents selected from the group consisting of lower alkyl, hydroxy, lower alkoxy and halogen; $R_2$ is hydrogen or lower alkyl; the radicals $R_3$, $R_4$ and $R_6$ are hydrogen; and each of $R_5$ and $R_7$, independently of the other, is hydrogen, lower alkyl or hydroxy; with an acid [PA] that is as defined above, for example one of the acids defined above as being important, for example one of the acids defined as being very, important: or tautomers thereof.

Most especially preferred are the acid addition salts of bases of formula I wherein A is a direct bond; X is a radical —C(=NH)—$NH_2$; Z is NH; $R_1$ is hydrogen or one or two substituents selected from the group consisting of lower alkyl, hydroxy and lower alkoxy; the radicals $R_2$, $R_3$ and $R_a$ are hydrogen; and $R_5$ is hydrogen or hydroxy; with an acid [PA] that is as defined above, for example one of the acids defined above as being important, especially one of the acids defined as being very important; or tautomers thereof.

As sub-groups of a group of acid addition salts of bases of formula I with acids [PA], attention is drawn to:

(a) acid addition salts of bases of formula I wherein A is a direct bond; (b) acid addition salts of bases of formula I wherein X is a radical —C(=NH)—$NH_2$; (c) acid addition salts of bases of formula I wherein Z is NH, $R_4$ is hydrogen, and $R_5$ is hydrogen or hydroxy; and (d) acid addition salts of bases of formula I wherein $R_1$ and $R_2$ are hydrogen; each of the other radicals being as defined; with acids [PA] selected from one of the groupings mentioned above, for example from the acids defined above as being very important; or tautomers thereof.

The invention relates more especially to the acid addition salts of bases of formula I wherein A is a direct bond; X is a radical —C(=NH)—$NH_2$; Z is NH; and each of $R_1$, $R_2$, $R_3$, $R_4$ and $R_5$ is hydrogen; and [PA] is selected from the above-mentioned acids, or is preferably one of the acids defined above as being important, for example one of the acids defined as being very important, for example an acid selected from N-cyclohexylsulfamic acid, octanoic acid, salicylic acid and benzenesulfonic acid, such as salicylic acid.

The invention relates more especially also to the acid addition salts of bases of formula I wherein A is a direct bond; X is a radical —C(=NH)—$NH_2$; Z is NH; and each of $R_1$, $R_2$, $R_3$, $R_4$ and $R_5$ is hydrogen; and [PA] is preferably one of the acids defined above as being very important, especially selected from tartaric acid, more especially L-tartaric acid, lactic acid and citric acid.

Most strongly preferred are the acid addition salts of bases of formula I mentioned in the Examples with an acid [PA].

The compounds of formula I can be prepared in a manner known per se, for example by (a) condensing a compound of formula II

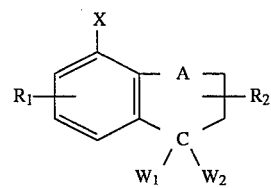

wherein the group $CW_1W_2$ is carbonyl, functionally modified carbonyl or protected carbonyl and A, X, $R_1$ and $R_2$ are as defined for formula I, or a salt thereof, if salt-forming groups are present, with an amine of formula III

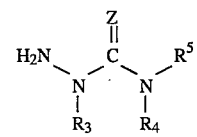

wherein Z, $R_3$, $R_4$ and $R_5$ are as defined for formula I, or a salt thereof, or (b) in a compound of formula IV

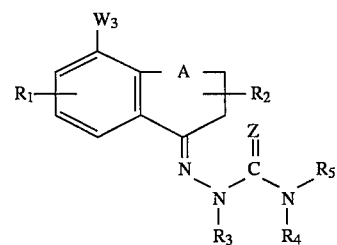

wherein $W_3$ is a radical that can be converted into a group X in formula I and A, Z, $R_1$, $R_2$, $R_3$, $R_4$ and $R_5$ are as defined for formula I, or a salt thereof, convening the radical $W_3$ into the group X; and, if desired, convening a resulting compound of formula I into a different compound of formula I and/or, if desired, convening a resulting salt into the free compound or into a different salt and/or, if desired, convening a resulting free compound of formula I having salt-forming properties into a salt.

In the following, more detailed description of processes a)-b), the symbols A, X, Y, Z and $R_1$–$R_9$ are each as defined for formula I, unless otherwise indicated.

Process (a):

Examples of functionally modified or protected carbonyl $CW_1W_2$ that may be mentioned are: di-lower alkoxymethyl, $C_1$–$C_2$alkylenedioxymethyl, dihalomethyl, di-lower alkylthiomethyl or $C_1$–$C_2$alkylenedithiomethyl.

The group $CW_1W_2$ in compounds of formula II is preferably in the form of free carbonyl.

The condensation reaction according to process (a) is carried out under conditions known per se for the formation of hydrazones. It is preferably acid-catalysed. In compounds of formula II, suitable protected carbonyl groups $CW_1W_2$ are those which are convened into free carbonyl under the conditions of the condensation.

For the preparation of compounds of formula I wherein $R_5$ is amino it is advisable to use the compound of formula III in excess.

The intermediates of formula II wherein Y in the radical X is NH are obtained, for example, by first converting a compound of formula V

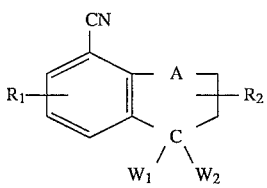

(V)

by treatment with hydrogen sulfide into the corresponding thiocarboxamide [—C(=S)—NH$_2$]. The latter can also be obtained by a different method starting from the analogous carboxamide [—C(=O)—NH$_2$], for example by reaction with the Lawesson reagent [2,4-bis-(4-methoxyphenyl)-2,4-dithioxo-1,3,2,4-dithiadiphosphetane]. The thiocarboxamides are S-alkylated, for example with lower alkyl iodide or tri-lower alkyloxonium tetrafluoroborate, and thus converted into imino-lower alkylthio ester hydroiodides [—C(=NH)—S-alkyl.HI] or tetrafluoroborates, respectively, which can readily be convened by reaction with ammonia or amines of the formula NHR$_6$R$_7$ into the desired carboximide amides of formula II [see S. Patai (Ed.), The Chemistry of Amidines and Imidates, Wiley, London etc. 1975, p 303–304].

The preparation of the carboxamides of formula II from the cyano compounds of formula V proceeds analogously to the preparation of carboxamides of formula I from cyano compounds of formula IV described below under process (b) and is described in detail there.

In a further possible method of preparing compounds of formula II, a compound of formula V, wherein the group CW$_1$W$_2$ is as defined for formula II, is treated, for example, with ethanol and hydrochloric acid in, for example, chloroform or diethyl ether, to form the corresponding iminoethyl ester hydrochloride which can be convened, for example by reaction with ammonia or a primary or secondary amine of the formula NHR$_6$R$_7$ and, for example, methanol, into the desired carboximide amide of formula II. In some cases, however, this method may not work as a result of sterical hindrance by the groups A and R$_1$.

The starting compounds of formula V are known per se or are prepared analogously to the known compounds.

The compounds of formula V can be prepared, for example, by intramolecular Friedel-Crafts acylation of ω-phenyl-lower alkanoic acids of formula VI

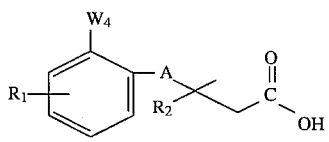

(VI)

wherein W$_4$ is cyano or a cyano precursor, or acid derivatives thereof, for example acid chlorides or acid anhydrides. In the case of free acids, the catalyst used may be, for example, polyphosphoric acid, and in the case of acid chlorides or anhydrides the catalyst may be, for example, AlCl$_3$.

In this reaction it is preferable to use compounds of formula VI wherein W$_4$ is not cyano but a cyano precursor, for example halogen, especially bromine, or protected amino, for example acetylamino. After the cyclisation step, the cyano precursors can then be convened into cyano in a manner known per se, for example in the case of bromine by reaction with copper(I) cyanide or in the case of acetylamino by removal of the acetyl protecting group, diazotization and reaction with copper(I) cyanide.

Compounds of formula V wherein the group CW$_1$W$_2$ is carbonyl can also be prepared, for example, by oxidation, for example with chromium trioxide (CrO$_3$), from the corresponding non-carbonyl compounds of formula VII

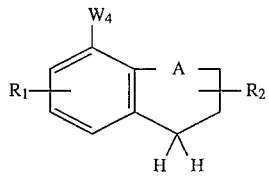

(VII)

wherein W$_4$ is cyano or a cyano precursor as defined above. If a cyano precursor is used, it should again be converted into cyano after the oxidation is complete, for example as indicated above.

In a further possible method of preparing the compounds of formula V wherein the group CW$_1$W$_2$ is carbonyl, compounds of formula H wherein X is hydrogen are used as starting materials and the cyano group is introduced, for example, by using a reaction sequence analogous to that in U.S. Pat. No. 3,956,363, Example 10, which consists of nitration, reduction of the nitro group to amino, diazotization and reaction with copper(I) cyanide (Sandmeyer reaction).

The preparation of aminoguanidines, aminoureas and aminothioureas of formula III is known per se. Amino(thio-)ureas [≙ semi(thio)carbazides] are prepared, for example, in an analogous manner to corresponding simple (thio-)ureas. For example, instead of an amine the corresponding hydrazine of the formula H$_2$N—NHR$_3$ is used and is reacted, for example, with an isocyanate of the formula R$_4$N=C=O or R$_5$N=C=O, an isothiocyanate of the formula R$_4$N=C=S or R$_5$N=C=S, a carbamoyl chloride of the formula R$_4$R$_5$N—COCl or a thiocarbamoyl chloride of the formula R$_4$R$_5$N—CSCl. Furthermore, it is also possible, for example, to react a hydrazine of the formula H$_2$N—NHR$_3$ with an acylisothiocyanate, for example acetylisothiocyanate, followed by acid hydrolysis.

Aminoguanidines of formula III wherein Z is NR$_9$ and R$_3$, R$_4$, R$_5$ and R$_9$ are as defined for formula I, are known per se and can be prepared, for example, from corresponding aminothioureas of formula III by converting the latter by alkylation, for example with an alkyl tosylate or halide, into the corresponding S-alkylisothiouronium salts which are then reacted with an amine of the formula NHR$_4$R$_5$.

Process (b):

In the intermediates of formula IV, W$_3$ is, for example, free or functionally modified carboxy, especially halocarbonyl, cyano, imino-lower alkoxycarbonyl or imino-lower alkylthiocarbonyl, or also thiocarbamoyl.

For the preparation of amidines of formula I (Y≙NR$_8$) the group W$_3$ in a compound of formula IV can be, for example: an acid addition salt of an imino-lower alkyl ester (≙ imino-lower alkyl ether) or imino-lower alkylthio ester, for example —C(=NH)—OC$_2$H$_5$. HCl or—C(=NH)—SC$_2$H$_5$.HI, or cyano.

The reaction of an imino-lower alkyl ester of formula IV (in salt form) with ammonia or primary or secondary amines results in the unsubstituted or mono- or di-substituted amidines of formula I. Cyano compounds of formula IV can be convened, for example by reaction with an alkali metal amide, for example KNH$_2$, or by reaction with a primary or secondary (di-)lower alkylammonium halide, for example $^⊕$NH$_3$CH$_3$Cl$^⊖$, into an unsubstituted or mono- or di-substituted amidine of formula I.

For the preparation of carbamoyl compounds of formula I (Y≙O) the group W$_3$ in a compound of formula IV may be, for example: carboxy, halocarbonyl (for example —COCl), lower alkoxycarbonyl or cyano. The formation of unsubstituted or mono- or di-substituted carbamoyl compounds of formula I from corresponding intermediates of formula IV wherein $W_3$ is carboxy, halocarbonyl or lower alkoxycarbonyl, by reaction with ammonia or primary or secondary amines is known per se. Intermediates of formula IV wherein $W_3$ is cyano can be convened, for example by partial hydrolysis, in the manner of a Graf-Ritter reaction, or by way of carboxylic acid ester imide salts, into unsubstituted or mono- or di-substituted carbamoyl compounds of formula I. The conditions for the hydrolysis of the cyano intermediates can be so chosen that the reaction is interrupted at the amide stage. Especially suitable for this purpose is hydrolysis with acids, for example with 80% sulfuric acid (with heating), polyphosphoric acid (at 110°–150° C.), hydrogen bromide/glacial acetic acid (at room temperature, in the presence of formic acid or without a further solvent) or HCl gas in ethereal solution followed by the addition of water or aqueous hydrochloric acid, or reaction with boron halides.

Using the Graf-Ritter reaction it is also possible to prepare N-substituted amides from nitriles of formula IV. For this purpose the nitriles are reacted in the presence of a strong acid, especially 85–90% sulfuric acid, or alternatively polyphosphoric acid, formic acid, boron trifluoride or other Lewis acids, but not aluminium chloride, with compounds capable of forming carbenium ions in the acidic medium, that is to say, for example, with olefins, such as propylene, or alcohols, such as ethanol.

The carboxylic acid ester imides are obtained, for example, by acid-catalysed addition of alcohols to the nitriles of formula IV. The amides are obtained from the ester imides in the manner of a Pinner cleavage by thermal decomposition of the ester imide salts at temperatures above approximately 80° C.

Compounds of formula IV wherein $W_3$ is cyano can be prepared, for example, by reacting a compound of formula V with a compound of formula III in accordance with process a). From compounds of formula IV wherein $W_3$ is cyano it is possible to prepare, in a manner known per se or as described above, the other compounds of formula IV wherein $W_3$ is free carboxy or carboxy functionally modified in some other way.

Compounds of formula I wherein X is a radical —C(=NH)—$NR_6R_7$ can also be obtained by reacting compounds of formula IV wherein $W_3$ is a radical —C(=S)—$NH_2$, with S-alkylation, for example with tri-lower alkyloxonium tetrafluoroborate, and by subsequent reaction with ammonia or an amine of the formula $NHR_6R_7$ or a corresponding ammonium salt, for example the chloride.

Compounds of formula I can be convened into different compounds of formula I.

For example, compounds of formula I wherein X is a radical —C(=S)—$NH_2$ can be convened by S-alkylation, for example with m-lower alkyloxonium tetrafluoroborate, and subsequent reaction with ammonia or an amine of the formula $NHR_6R_7$, or especially a corresponding ammonium salt thereof, into compounds of formula I wherein X is a radical —C(=NH)—$NR_6R_7$.

Compounds of formula I wherein X is an N-hydroxyamidino radical —C(=$NR_8$)—NHOH can be convened, for example by reaction with iron pentacarbonyl [Fe(CO)$_5$], into other compounds of formula I wherein X is an analogous amidino radical —C(=$NR_8$)—$NH_2$ (see, for example, J. Chem. Soc. Chem. Commun. 1975, 761).

Free compounds of formula I obtainable in accordance with the process having salt-forming properties can be convened into their salts in a manner known per se; compounds having basic properties can be converted into their salts, for example, by treatment with acids or suitable derivatives thereof, and compounds having acidic properties can be convened into their salts, for example, by treatment with bases or suitable derivatives thereof.

Especially, free compounds of formula I that have salt-forming properties and that are obtainable in accordance with the process can be convened in a manner known per se into their salts: for example, compounds having basic properties can be convened by treatment with acids, either with the protic acids [PA] themselves or preferably with other protic acids, for example organic acids that do not fall within the definition of [PA], such as formic acid, acetic acid and methanesulfonic acid, or inorganic acids, such as sulfuric acid, hydrohalic acids, such as HF, HCl, HBr or HI, also hydrazoic acid or phosphoric acid. Hydrohalic acids are especially preferred. The reaction takes place analogously for the preparation of acid addition salts of bases of formula I with acids [PA].

The acid addition salts of bases of formula I, especially those with protic acids other than [PA], can also be convened into the free compounds. That can be effected, for example, by conversion into the free base, for example by reaction of the salt of a compound of formula I used as starting material with a hydroxy base, such as an alkali metal hydroxide, for example NaOH or KOH, in aqueous solution in the presence or, preferably, absence of an organic solvent, as defined mentioned above, also by dialysis, using ion exchangers or by gel chromatography.

As a result of the close relationship between the compounds of formula I in free form and in the form of salts, hereinabove and hereinbelow any reference to the free compounds or their salts is to be understood as including the corresponding salts or free compounds, respectively, as appropriate add expedient.

Owing to the close relationship between the compounds of formulae II, III, IV and also V, VI and VII in free form and, insofar as the mentioned compounds contain salt-forming groups, in the form of salts, hereinbefore and hereinafter the free compounds and their salts are also to be understood as being the corresponding salts, for example acid addition salts or also salts with bases, and the free compounds, respectively, where appropriate and where the context so allows.

The preparation of salts, for example of the compounds of formulae II, III and IV having salt-forming groups, is carried out analogously to the preparation of salts of the compounds of formula I (Process c) below).

The compounds, including their salts, can also be obtained in the form of hydrates, or their crystals may include, for example, the solvent used for crystallization.

Mixtures of isomers obtainable in accordance with the invention can be separated into the individual isomers in a manner known per se; racemates can be separated, for example, by the formation of salts with optically pure salt-forming reagents and separation of the diastereoisomeric mixture so obtainable, for example by fractional crystallization.

The above-mentioned reactions can be carried out under reaction conditions known per se, in the absence or, usually, in the presence of solvents or diluents, preferably those solvents or diluents which are inert towards the reagents used, and are solvents therefor, in the absence or presence of catalysts, condensation agents or neutralising agents, and, depending upon the nature of the reaction and/or the reactants, at reduced, normal or elevated temperature, for example in a temperature range of from approximately −70° C. to approximately 190° C., preferably from approximately −20° C. to approximately 150° C., for example at the boiling point of the solvent used, especially in the reaction mixture concerned, or at room temperature, under atmospheric pressure or in a closed vessel, where appropriate under pressure, and/or in an inert atmosphere, for example under a nitrogen atmosphere.

The protic acids [PA] are known, can be prepared in accordance with processes known per se or are commercially available.

In the process of the present invention it is preferable to use those starting materials which result in the compounds described at the beginning as being especially valuable.

In the process of the present invention, it is preferable to use those starting materials that lead to the acid addition salts described at the beginning as being especially valuable.

The invention relates also to those forms of the process in which a compound obtainable as intermediate at any stage of the process is used as starting material and the remaining process steps are carried out, or in which a starting material is formed under the reaction conditions or is used in the form of a derivative, for example a salt thereof.

The invention relates also to those forms of the process in which a compound obtainable as intermediate at any stage of the process is used as starting material and the remaining process steps are carried out, or in which a starting material is formed under the reaction conditions or is used in the form of a derivative, for example a salt, thereof.

Pharmaceutical compositions

The present invention relates also to pharmaceutical compositions that comprise one of the pharmacologically active compounds of formula I or especially one of the pharmacologically active acid addition salts of a base of formula I with an acid [PA] as active ingredient. Compositions for enteral, especially oral, and for parenteral administration are especially preferred. The compositions comprise the active ingredient on its own or, preferably, together with a pharmaceutically acceptable carrier. The dosage of the active ingredient depends upon the disease to be treated and upon the species, its age, weight and individual condition, and also upon the mode of administration.

The pharmaceutical compositions comprise from approximately 0.1% to approximately 95% active ingredient, dosage forms in single dose form preferably comprising from approximately 1% to approximately 90% active ingredient and dosage forms that are not in single dose form preferably comprising from approximately 0.1% to approximately 20% active ingredient. Unit dose forms, such as dragées, tablets or capsules, comprise from approximately 1 mg to approximately 500 mg of active ingredient.

The pharmaceutical compositions of this invention are prepared in a manner known per se, for example by means of conventional mixing, granulating, confectioning, dissolving or lyophilising processes. For example, pharmaceutical compositions for oral use can be obtained by combining the active ingredient with one or more solid careers, optionally granulating a resulting mixture, and, if desired, processing the mixture or granules, if necessary with the addition of additional excipients, to form tablets or dragée cores.

Suitable careers are especially fillers, such as sugars, for example lactose, saccharose, mannitol or sorbitol, cellulose preparations and/or calcium phosphates, for example tricalcium phosphate or calcium hydrogen phosphate, also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, cross-linked polyvinylpyrrolidone, alginic acid or a salt thereof, such as sodium alginate.

Additional excipients are especially flow conditioners and lubricants, for example silicic acid, talc, stearic acid or salts thereof, such as magnesium or calcium stearate, and/or polyethylene glycol, or derivatives thereof.

Dragée cores can be provided with suitable, optionally enteric, coatings, there being used inter alia concentrated sugar solutions which may contain gum arabic, talc, polyvinylpyrrolidone, polyethylene glycol and/or titanium dioxide, or coating solutions in suitable organic solvents or solvent mixtures, or, for the production of enteric coatings, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Orally administrable pharmaceutical compositions also include dry-filled capsules consisting of gelatin, and also soft, sealed capsules consisting of gelatin and a plasticiser, such as glycerol or sorbitol. The dry-filled capsules may contain the active ingredient in the form of granules, for example in admixture with fillers, such as corn starch, binders and/or glidants, such as talc or magnesium stearate, and optionally stabilisers. In soft capsules, the active ingredient is preferably dissolved or suspended in suitable liquid excipients, such as fatty oils, paraffin oil or liquid polyethylene glycols, to which stabilisers may also be added.

Other oral dosage forms are, for example, syrups prepared in customary manner which comprise the active ingredient, for example, in suspended form and in a concentration of about 0.1% to 10%, preferably about 1%, or in a similar concentration that provides a suitable single dose, for example, when administered in measures of 5 or 10 ml. Also suitable are, for example, powdered or liquid concentrates for the preparation of shakes, for example in milk. Such concentrates may also be packaged in single dose quantities.

Suitable rectally administrable pharmaceutical compositions are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration there are especially suitable aqueous solutions of an active ingredient in water-soluble form, for example in the form of a water-soluble salt, or aqueous injection suspensions that contain viscosity-increasing substances, for example sodium carboxymethylcellulose, sorbitol and/or dextran, and, if desired, stabilisers. The active ingredient, optionally together with excipients, can also be in the form of a lyophilisate and can be made into a solution prior to parenteral administration by the addition of suitable solvents.

An isotonic solution for infusion can be prepared especially by the addition of suitable salts, such as NaCl, buffers, such as phosphate buffers, for example with sodium as counter-ion, and/or sugar alcohols, such as mannitol, it being optionally possible for others of the mentioned excipients also to be present.

Solutions such as are used, for example, for parenteral administration can also be used as infusion solutions.

The invention relates also to a method of treating the above-mentioned pathological conditions. The compounds of this invention can be administered prophylactically or therapeutically, preferably in the form of pharmaceutical compositions. In the case of an individual having a body weight of about 70 kg the daily dose administered is from approximately 1 mg to approximately 1000 mg, preferably approximately from 25 to 100 mg in the case of oral administration and approximately from 2 to 50 mg in the case of parenteral administration, of a compound of the present invention.

The invention relates also to a method of treating the above-mentioned diseased states, caused especially by a lack of S-adenosylmethionine decarboxylase-inhibition, which respond to treatment with an inhibitor of S-adenosylmethionine decarboxylase. The acid addition salts of the present invention, especially of bases of formula I and an acid [PA], may be administered prophylactically or therapeutically, especially in amounts that are suitable for inhibiting S-adenosylmethionine decarboxylase, and they are used preferably in the form of pharmaceutical compositions. In the case of a body weight of approximately 70 kg, a daily dose, especially one that is effective against the mentioned diseases, of from approximately 1 mg to approximately 1000 mg, preferably approximately from 25 to 100 mg in the case of oral administration or approximately from 2 to 50 mg in the case of parenteral administration, of an acid addition salt of the present invention is administered, for example to a warm-blooded animal, such as a human, that is in need of such treatment because it is suffering from a protozoa infection or from tumours.

The invention relates also to a pharmaceutical composition that is suitable for administration to a mammal, for example a human, for the prevention or treatment of a disease that responds to treatment with an inhibitor of S-adenosylmethionine decarboxylase, especially a tumour disease or a protozoa infection, which composition comprises an amount of an acid addition salt of formula I, or tautomers thereof, of the present invention, especially of bases of formula I and an acid [PA], that is effective in the inhibition of S-adenosylmethionine decarboxylase, and a pharmaceutically acceptable carrier.

The following Examples illustrate the present invention; temperatures are given in degrees Celsius. The following abbreviations are used: abs.=absolute (anhydrous); $D_2O$= deuterised water;, DMF=N,N-dimethylformamide; DMSO-$d_6$=perdeuterised dimethyl sulfoxide; ether=diethyl ether, ethyl acetate=acetic acid ethyl ester; IR=infrared spectroscopy; m.p.=melting point; THF=tetrahydrofuran; MS (FAB)=mass spectrum ("Fast Atom Bombardment")

EXAMPLE 1

4-Amidino-1-indanone-2'-amidinohydrazone dihydrochloride

A solution of 3.8 g (27.9 mmol) of aminoguanidine hydrogen carbonate in 200 ml of water and 14.7 ml of 2N hydrochloric acid is heated to 60° and, with stirring, a solution of 5.85 g (27.8 mmol) of 4-amidino-1-indanone hydrochloride in 200 ml of methanol is added thereto within a period of 30 minutes. The reaction mixture is boiled at reflux for 24 hours and, after cooling, concentrated to dryness by evaporation. The residue is suspended in 50 ml of ethanol, filtered, washed with ethanol and ether and dried, yielding the title compound containing 1 mol of water of crystallization, m.p.>330°; MS(FAB): $(M+H)^+=231$; $^1$H-NMR ($D_2O$): $\delta=8.08$ (d,1H); 7.75 (d,1H); 7.58 (t,1H); 3.35 (m,2H); 2.96 (m,2H).

The starting compounds are prepared as follows:
(a) 4-Thiocarbamoyl-1-indanone

A solution of 12.1 g (77 mmol) of 4-cyano-1-indanone [Coll. Czechoslov. Chem. Commun. 43, 3227 (1978)] in 220 ml of pyridine and 10.6 ml (77 mmol) of triethylamine is saturated with hydrogen sulfide for 3 hours at 40° and then stirred for a further 16 hours at the same temperature. After cooling, the reaction mixture is concentrated to dryness by evaporation and then 300 ml of water are added to the residue. The yellow product that crystallises out is filtered off with suction, washed with water, dried and recrystallised from ethyl acetate, yielding starting compound (a), m.p. 197° (decomp.).

b) 4-Amidino-1-indanone hydrochloride 10.8 g (54 mmol) of triethyloxonium tetrafluoroborate are added at room temperature under argon to a solution of 9.8 g (51.3 mmol) of 4-thiocarbamoyl-1-indanone in 500 ml of absolute methylene chloride. After 16 hours a mixture of 4.2 g of potassium carbonate and 4.2 ml of water is added to the reaction solution. The mixture is then stirred briefly and filtered, and the filtrate is washed with water. The organic phase is dried over magnesium sulfate, filtered and concentrated by evaporation. The resulting crude ethylthioimino ether is dissolved in 160 ml of absolute ethanol; 3.3 g (60 mmol) of ammonium chloride are added and the mixture is heated at reflux for 20 hours. After cooling, the reaction mixture is concentrated to dryness by evaporation. Starting compound (b) is purified by chromatography on 1000 ml of Amberlite® ER-180 resin (water as eluant) and recrystallised from ethanol/ether, m.p. 215°–218° (decomp.).

EXAMPLE 2

4-Amidino-1-indanone-2'-(N-hydroxyamidino)-hydrazone dihydrochloride

A solution of 394 mg (1.5 mmol) of 1-amino-3-hydroxyguanidine-4-toluenesulfonate in 6 ml of water and 0.75 ml (1.5 mmol) of 2N hydrochloric acid is added to a solution of 316 mg (1.5 mmol) of 4-amidino-1-indanone hydrochloride (Example 1b) in 7 ml of methanol, and the mixture is heated at reflux for 2 hours and stirred at room temperature for 16 hours. The reaction mixture is concentrated by evaporation and the residue is purified by chromatography (Pharmacia column SR-28-100) on silica gel OPTI-UP $C_{12}$ (water as eluant, 5 ml fractions, throughflow rate 27.5 ml/h). The contents of fractions 58–78 are combined and concentrated by evaporation, and the residue is crystallised from ethanol, yielding the title compound in the form of wax-like crystals, MS (FAB): $(M+H)^+=247$; $^1$H-NMR ($D_2O$): $\delta=8.06$ (d,1H); 7.73 (d,1H); 7.58 (t,1H); 3.36 (m,2H); 2.98 (m,2H).

EXAMPLE 3

5-Amidino-1-tetralone-2'-amidinohydrazone dihydrochloride 0.675 g (3 mmol) of 5-amidino-1-tetralone hydrochloride is added to a solution of 0.41 g (3 mmol) of aminoguanidine hydrogen carbonate in 31.5 ml of 0.1N hydrochloric acid and the mixture is heated at reflux for 72 hours. After cooling, the mixture is concentrated to dryness by evaporation and the title compound is recrystallised from methanol/ether, m.p. >250°; MS (FAB): $(M+H)^+=245$; $^1$H-NMR (DMSO-$d_6$): $\delta=11.3$ (s,1H); 9.5 (m,4H); 8.65 (d,1H); 7.92 (m,3H); 7.52 (d,1H); 7.46 (t,1H); 2.7–2.85 (m,4H); 1.9 (m,4H).

The starting compounds are prepared as follows:
(a) 5-Cyano-1-tetralone 0.41 g (4.5 mmol) of copper(I) cyanide is added to a solution of 1.0 g (4.4 mmol) of 5-bromo-1-tetralone [J. Org. Chem. 49, 4226 (1984)] in 1.3 ml of DMF and stirred for 6 hours at 160°. The reaction mixture is then cooled to 80° and a solution of 1.6 g of iron(III) chloride hexahydrate in 2.5 ml of water and 0.44 ml of concentrated hydrochloric acid is added. The reaction mixture is stirred for 45 minutes, cooled, diluted with water and extracted with toluene. The organic phase is washed with water, dried over magnesium sulfate, filtered and concentrated by evaporation, yielding starting compound (a) in the form of yellowish-orange crystals. IR ($CH_2Cl_2$): 2220, 1690 $cm^{-1}$; $^1$H-NMR ($CDCl_3$): δ=8.26 (q,1H); 7.81 (q,1H); 7.43 (t,1H); 3.21 (t,2H); 2.72 (t,2H); 2.23 (m,2H).

(b) 5-Thiocarbamoyl-1-tetralone

Analogously to Example 1a, 10.6 g (62 mmol) of 5-cyano-1-tetralone in 200 ml of pyridine and 8.6 ml of methylamine are treated with hydrogen sulfide and worked up, yielding starting compound (b) in the form of yellow crystals, m.p. 200°–205°.

(c) 5-Amidino-1-tetralone hydrochloride

Analogously to Example 1b, 8.6 g (42 mmol) of 5-thiocarbamoyl-1-tetralone are treated with 8.8 g (44 mmol) of triethyloxonium tetrafluoroborate and 2.6 g (49 mmol) of ammonium chloride, yielding starting compound (c) in the form of slightly pink crystals, MS(FAB):$(M+H)^+$=189.

EXAMPLE 4

4-Thiocarbamoyl-1-indanone-2'-amidinohydrazone hydrochloride 1.36 g (10 mmol) of aminoguanidine hydrogen carbonate and 10 ml of 2N hydrochloric acid are added to a solution of 1.9 g (10 mmol) of 4-thiocarbamoyl-1-indanone (Example 1a) in 50 ml of ethanol and the mixture is heated at reflux for 24 hours. After cooling, the reaction mixture is concentrated to dryness by evaporation, yielding the title compound.

EXAMPLE 5

4-Amidino-1-indanone-2'-amidinohydrazone dihydrochloride

Analogously to Example 1b, 4-thiocarbamoyl-1-indanone-2'-amidinohydrazone hydrochloride (Example 4) is reacted with triethyloxonium tetrafluoroborate and ammonium chloride, yielding the title compound, m.p.>330°; MS (FAB): $(M+H)^+$=231; $^1$H-NMR ($D_2O$): δ=8.08 (d,1H); 7.75 (d,1H); 7.58 (t,1H); 3.35 (m,2H); 2.96 (m,2H).

EXAMPLE 6

4-Amidino-1-indanone-2'-amidinohydrazone dihydrochloride 1.2 ml of a 1N sodium methoxide solution in methanol are added to a solution of 0.26 g (1 mmol) of 4-cyano-1-indanone-2'-amidinohydrazone hydrochloride in 5 ml of absolute methanol and the mixture is heated at reflux for 16 hours. After cooling, 0.16 g (3 mmol) of solid ammonium chloride is added to the reaction mixture which is then stirred for 1 hour at 60°. The reaction mixture is then concentrated by evaporation and the residue is crystallised from dilute ethanol, yielding the title compound, m.p.>330°.

The starting compound is prepared as follows:

(a) 4-Cyano-1-indanone-2'-amidinohydrazone hydrochloride

Analogously to Example 1,314 mg (2 mmol) of 4-cyano-1-indanone are dissolved in 20 ml of methanol; a solution of 272 mg (2 mmol) of aminoguanidine hydrogen carbonate in 9 ml of water and 1 ml of 2N hydrochloric acid is added and the mixture is stirred at reflux for 4 days. After cooling, the reaction mixture is concentrated to dryness by evaporation and the residue is crystallised from water, yielding starting compound (a), m.p. >230°; $^1$H-NMR (DMSO-$d_6$/$D_2O$): δ=8.16 (d,1H); 7.9 (d,1H); 7.55 (t,1H); 3.28 (m,2H); 2.9 (m,2H); IR(Nujol): 2190 $cm^4$ (CN).

EXAMPLE 7

4-(N-Hydroxyamidino)-1-indanone-2'-amidinohydrazone dihydrochloride 0.2 g (3 mmol) of hydroxylamine hydrochloride are suspended in 1 ml of absolute ethanol, and 2 ml of a 1N sodium ethoxide solution in ethanol are added. This mixture is stirred for 1 hour and filtered. A solution of 0.26 g (1 mmol) of 4-cyano-1-indanone-2'-amidinohydrazone hydrochloride (Example 6a) in 2 ml of water is added to the filtrate, and the mixture is heated at reflux for 6 hours. After cooling, the reaction mixture is concentrated by evaporation and the title compound is crystallised from water, m.p.>250°; $^1$H-NMR (DMSO-$d_6$+$D_2O$): δ=8.12 (m,1H); 7.55 (m,2H); 3.22 (m,2H); 2.83 (m,2H).

EXAMPLE 8

4-Amidino-2-methyl-1-indanone-2'-amidinohydrazone dihydrochloride

Analogously to Example 1, the title compound is prepared from 4-cyano-2-methyl-1-indanone (see U.S. Pat. No. 3,956,363).

EXAMPLE 9

5-Amidino-6-methoxy-1-tetralone-2'-amidinohydrazone dihydrochloride

Analogously to Example 1, the title compound is prepared from 5-cyano-6-methoxy-1-tetralone [Chem. Pharm. Bull. 31, 2329 (1983)].

EXAMPLE 10

4-Amidino-6-methyl-1-indanone-2'-amidinohydrazone dihydrochloride

Analogously to Example 3, the title compound is prepared from 4-bromo-6-methyl-1-indanone (Bull. Soc. Chim. France 1964, 3103), m.p.>250° C.; MS(FAB): $(M+H)^+$= 245; $^1$H-NMR ($D_2O$): δ=7.89 (s, 1H); 7.62 (s, 1H); 3.34 (t, 2H); 2.96 (t, 2H); 2.45 (s, 3H).

EXAMPLE 11

4-Amidino-6-methoxy-7-methyl-1-indanone-2'-amidinohydrazone dihydrochloride

Analogously to Example 3, the title compound is prepared from 4-bromo-6-methoxyl-7-methyl-1-indanone (J. Chem. Soc. Perkin Trans. 1 1974, 1911).

EXAMPLE 12

4-Amidino-6,7-dimethyl-1-indanone-2'-amidinohydrazone dihydrochloride

Analogously to Example 3, the title compound is prepared from 4-bromo-6,7-dimethyl-1-indanone [J. Het. Chem. 24, 677 (1987)].

EXAMPLE 13

4-Amidino-7-hydroxy-3-methyl-1-indanone-2'amidinohydrazone dihydrochloride

Analogously to Example 3, the title compound is prepared from 4-bromo-7-hydroxy-3-methyl-1-indanone [Indian J. Chem. Sect. B 24B, 1061 (1985)].

EXAMPLE 14

4-(Methylamidino)-1-indanone-2'-amidinohydrazone dihydrochloride

Analogously to Example 1b, 4-thiocarbamoyl-1-indanone-2'-amidinohydrazone hydrochloride (Example 4) is reacted with triethyloxonium tetrafluoroborate and methylammonium chloride, yielding the title compound.

EXAMPLE 15

4-Amidino-1-indanone-2'-amidinohydrazone dihydrochloride 9.45 g (44.9 mmol) of 4-amidino-1-indanone hydrochloride (see Example 1b) are added to a solution of 6.12 g (45 mmol) of aminoguanidine hydrogen carbonate in 100 ml of water and 46 ml of 1N hydrochloric acid and the mixture is stirred for 24 hours at 24°. The product that crystallises out is filtered off with suction, washed with a small amount of water and recrystallised from 300 ml of water, yielding the title compound containing 1 mol of water of crystallization, m.p.>330°; MS(FAB): $(M+H)^+$=231; $^1$H-NMR ($D_2O$): $\delta$=8.08 (d,1H); 7.75 (d,1H); 7.58 (t,1H); 3.35 (m,2H); 2.96 (m,2H).

EXAMPLE 16

4-Amidino-2-methyl-1-indanone-2'-amidinohydrazone dihydrochloride

A solution of 1.0 g (5.0 mmol) of 4-amidino-2-methyl-1indanone hydrochloride and 0.68 g (5.0 mmol) of aminoguanidine hydrogen carbonate in 10 ml of 0.5N hydrochloric acid is stirred for 120 hours at 25°. The product that crystallises out is filtered off with suction, washed with a small amount of water and dried, yielding the title compound, m.p.>250°; MS(FAB): $(M+H)^+$=245; $^1$H-NMR ($D_2O$): $\delta$=7.95 (d,1H); 7.66 (d,1H); 7.48 (t,1H); 3.45 (m,2H); 2.85 (d,1H); 1.12 (d,3H).

The starting compounds are prepared as follows:
(a) 4-Thiocarbamoyl-2-methyl-1-indanone Analogously to Example 1a, 11.1 g (65 mmol) of 4-cyano-2-methyl-1-indanone [see U.S. Pat. No. 3,956,363] in 200 ml of pyridine and 9.7 ml of triethylamine are treated with hydrogen sulfide and worked up, yielding starting compound (a) in the form of yellow crystals, m.p. 195°–198° (decomp.); $^1$H-NMR (DMSO-$d_6$): $\delta$=9.61 (s,1H); 7.71 (m,2H); 7.48 (m,1H); 3.48 (m,1H); 2.81 (m,2H); 1.23 (s,3H); 1.19 (s,3H).

(b) 4-Amidino-2-methyl-1-indanone hydrochloride

Analogously to Example 1b, 10.2 g (50 mmol) of starting compound (a) are treated with 11.0 g (55 mmol) of triethyloxonium tetrafluoroborate and 3.2 g (60 mmol) of ammonium chloride, yielding starting compound (b) in the form of pink crystals. It is immediately reacted further.

EXAMPLE 17

4-Amidino-6,7-dimethyl-1-indanone-2'-amidinohydrazone dihydrochloride

Analogously to Example 1, the title compound is prepared from 4-amidino-6,7-dimethyl-1-indanone hydrochloride, m.p.>240° C.; MS (FAB): $(M+H)^{\oplus}$=259; $^1$H-NMR ($D_2O$): $\delta$=7.43 (s,1H); 3.12 (m,2H); 2.75 (m,2H); 2.43 (s,3H); 2.24 (s,3H).

The starting compounds are prepared as follows:
(a) 4-Cyano-6,7-dimethyl-1-indanone A mixture of 17.8 g (74.5 mmol) of 4-bromo-6,7-dimethyl-1-indanone [J. Het. Chem. 24, 677 (1987)] and 7.3 g (82 mmol) of copper(I) cyanide in 18 ml of DMF is stirred for 6 hours at 170°. The reaction mixture is then cooled to 100° and 200 ml of toluene and a solution of 31.2 g of iron(III) chloride hexahydrate in 47 ml of water and 8.2 ml of concentrated hydrochloric acid are added in succession thereto. The reaction mixture is stirred for 20 minutes at 70°, cooled and diluted with toluene and water. The organic phase is separated off, washed with water, a semi-saturated sodium hydrogen carbonate solution and again with water, dried and concentrated by evaporation. The residue is crystallised from ethyl acetate and ether and corresponds to starting compound (a). Beige crystals having a melting point of 160°–163° are obtained; IR ($CH_2C_{12}$): 2220, 1710 $cm^{-1}$.

(b) 4-Thiocarbamoyl-6,7-dimethyl-1-indanone

Analogously to Example 1a, 10 g (54.1 mmol) of starting compound (a) in 200 ml of pyridine and 7.5 ml of triethylamine are treated with hydrogen sulfide and worked up, yielding starting compound (b) in the form of yellow crystals, m.p. 207°–208°; $^1$H-NMR (DMSO-$d_6$): $\delta$=10.03 (s,1H); 9.49 (s,1H); 7.49 (s,1H); 3.12 (m,2H); 2.61 (m,2H); 2.54 (s,3H); 2.29 (s,3H).

(c) 4-Amidino-6,7-dimethyl-1-indanone hydrochloride

Analogously to Example 1b, 4.4 g (20 mmol) of starting compound (b) are treated with 4.26 g (21 mmol) of triethyloxonium tetrafluoroborate and 1.2 g (24 mmol) of ammonium chloride, yielding stating compound (c) in the form of beige crystals.

EXAMPLE 18

4-Amidino-6,7-dimethoxy-1-indanone-2'-amidinohydrazone dihydrochloride 0.73 g (2.7 mmol) of 4-amidino-6,7-dimethoxy-1-indanone hydrochloride is added to a solution of 0.4 g (3 mmol) of aminoguanidine hydrogen carbonate in 6 ml of 0.5N hydrochloric acid and the mixture is stirred for 24 hours at 50°. After cooling, the product that has crystallised out is filtered with suction, washed with a small amount of water and dried, yielding the title compound, m.p.>220°; MS(FAB): $(M+H)^+$=291; $^1$H-NMR ($D_2O$): $\delta$=7.45 (s,1H); 3.97 (s,6H); 3.27 (m,2H); 2.98 (m,2H).

The starting compounds are prepared as follows:
(a) 4-Cyano-6,7-dimethoxy-1-indanone A mixture of 6.57 g (24.2 mmol) of 4-bromo-6,7-dimethoxy-1-indanone [Can. J. Chem. 57, 1603 (1979)] and 2.5 g (28 mmol) of copper(I) cyanide in 7 ml of DMF is stirred for 5.75 hours at 170°. The reaction mixture is then cooled to 100° and then 70 ml of toluene and a solution of 9.7 g (36 mmol) of iron(III) chloride hexahydrate in 15.6 ml of water and 3.5 ml of concentrated hydrochloric acid are added in succession thereto. The reaction mixture is then stirred for 30 minutes at 80°, cooled and diluted with toluene and water. The organic phase is separated off, washed with water, a semi-saturated sodium hydrogen carbonate solution and again with water, dried and concentrated by evaporation. The residue is distilled at 150°–160°/0.1 mbar in a bulb tube still and corresponds to starting compound (a), m.p. 150°; IR ($CH_2Cl_2$): 2220, 1710 $cm^{-1}$; $^1$H-NMR ($CDCl_3$): $\delta$=7.33 (s,1H); 4.12 (s,3H); 3.90 (s,3H); 3.19 (m,2H); 2.76 (m,2H).

(b) 4-Thiocarbamoyl-6,7-dimethoxy-1-indanone

Analogously to Example 1a, 3.7 g (17 mmol) of starting compound (a) in 100 ml of pyridine and 2.4 ml of triethylamine are treated with hydrogen sulfide and worked up, yielding starting compound (b) in the form of bright yellow crystals, m.p. 196°–199°; $^1$H-NMR (DMSO-$d_6$): $\delta$=10.06 (s,1H); 9.50 (s,1H); 7.41 (s,1H); 3.84 (s,6H); 3.13 (m,2H); 2.63 (m,2H).

(c) 4-Amidino-6,7-dimethoxy-1-indanone hydrochloride

Analogously to Example 1b, 3.3 g (13 mmol) of starting compound (b) are treated with 2.8 g (14 mmol) of triethyloxonium tetrafluoroborate and 0.8 g (15 mmol) of ammonium chloride, yielding starting compound (c) in the form of beige crystals, m.p. 188° (with decomp.); $^1$H-NMR(DMSO-$d_6$): δ=9.4 (s,3H); 7.63 (s,1H); 3.92 (s,3H); 3.89 (s,3H); 3.18 (m,2H); 2.68 (m,2H).

EXAMPLE 19

4-Amidino-3-methyl-1-indanone-2'-amidinohydrazone dihydrochloride 300 mg (2.3 mmol) of aminoguanidine hydrogen carbonate in 4 ml of 0.5N hydrochloric acid are added to a solution of 300 mg (1.3 mmol) of 4-amidino-3-methyl-1-indanone hydrochloride in 6 ml of water and the mixture is stirred for 24 hours at 80°. The reaction mixture is cooled and concentrated by evaporation and the residue is purified by chromatography on 180 ml of Amberlite® ER-180 resin with water as eluant. The title compound is recrystallised from methanol/ether, m.p.>250°; $R_f$=0.18 (silica gel, methylene chloride/methanol/conc.ammonia 5:3:1); MS(FAB): $(M+H)^+$=245; $^1$H-NMR ($D_2O$): δ=7.97 (d,1H); 7.64 (d,1H); 7.49 (t,1H); 3.86 (m,1H); 3.17 (q,1H); 2.49 (d,1H); 1.24 (d,3H).

The starting compounds are prepared as follows:

(a) 4-Cyano-3-methyl-1-indanone

A mixture of 2.6 g (11.5 mmol) of 4-bromo-3-methyl-1-indanone [J. Org. Chem. 22, 1019 (1957)] and 1.14 g (12.7 mmol) of copper(I) cyanide in 2.5 ml of DMF is stirred for 6 hours at 170°. The reaction mixture is then cooled to 100°, and 50 ml of toluene and a solution of 4.5 g (16.5 mmol) of iron(III) chloride hexahydrate in 7 ml of water and 1.7 ml of concentrated hydrochloric acid are added in succession thereto. The reaction mixture is stirred for 20 minutes at 70°, cooled and diluted with toluene and water. The organic phase is separated off, washed with water, a semi-saturated sodium hydrogen carbonate solution and again with water, dried and concentrated by evaporation. The residue is distilled at 100°–120°/0.05 mbar in a bulb tube still and corresponds to starting compound (a), m.p. 109°–111°; IR ($CH_2Cl_2$): 2220, 1710 cm$^{-1}$; $^1$H-NMR ($CDCl_3$): δ=7.92 (m,2H); 7.52 (t,1H); 3.73 (m,1H); 3.03 (q,1H); 2.40 (q,1H); 1.55 (d,3H).

(b) 4-Thiocarbamoyl-3-methyl-1-indanone

Analogously to Example 1a, 1.45 g (8.47 mmol) of starting compound (a) in 25 ml of pyridine and 1.2 ml of triethylamine are treated with hydrogen sulfide and worked up, yielding starting compound (b) in the form of pale yellow crystals, m.p. 198°–200°; $^1$H-NMR (DMSO-$d_6$): δ=9.78 (s,1H); 7.65 (m,2H); 7.46 (m,1H); 3.98 (m,1H); 2.95 (q,1H); 2.26 (q,1H); 1.25 (d,3H).

(c) 4-Amidino-3-methyl-1-indanone hydrochloride

Analogously to Example 1b, 0.96 g (4.68 mmol) of starting compound (b) is treated with 1.0 g (4.93 mmol) of triethyloxonium tetrafluoroborate and 0.3 g (6 mmol) of ammonium chloride, yielding starting compound (c) in the form of beige crystals, $^1$H-NMR (DMSO-$d_6$): δ=9.59 (s,4H); 7.65 (m,2H); 7.46 (m,1H); 3.98 (m,1H); 2.95 (q,1H); 2.26 (q,1H); 1.25 (d,3H).

EXAMPLE 20

4-Amidino-1-indanone-2'-amidinohydrazone dihydrochloride

A mixture of 0.32 g (1 mmol) of 4-(N-hydroxyamidino)-1-indanone 2'-amidinohydrazone dihydrochloride (Example 7), 0.36 ml (2 mmol) of triethylamine and 0.2 g (1 mmol) of iron pentacarbonyl in 10 ml of absolute THF is boiled at reflux for 16 hours. The reaction mixture is then concentrated by evaporation and the residue is crystallised from dilute hydrochloric acid, yielding the title compound, m.p.>330°.

EXAMPLE 21

4-Amidino-2-ethyl-1-indanone-2'-amidinohydrazone dihydrochloride 3-(2-Bromophenyl)-2-ethylpropionic acid (German Patent 2 733 868) is cyclised with polyphosphoric acid at elevated temperature to form the corresponding 1-indanone and convened into the title compound analogously to Example 3. M.p.>250° C.; MS(FAB): $(M+H)^+$=259; $^1$H-NMR ($D_2O$): δ=7.96 (d,1H); 7.65 (d,1H); 7.48 (t,1H); 2.95–3.4 (m,3H); 1.3–1.8 (m,2H); 0.83 (t,3H).

EXAMPLE 22

4-Amidino-2-n-butyl-1-indanone-2'-amidinohydrazone dihydrochloride 3-(2-Bromophenyl)-2-n-butylpropionic acid (Geman Patent 2 733 868) is cyclised with polyphosphoric acid at elevated temperature to form the corresponding 1-indanone and convened into the title compound analogously to Example 3.

EXAMPLE 23

Capsules containing 0.25 g of active ingredient, for example one of the compounds of Examples 1 to 22, can be prepared as follows:

| Composition (for 5000 capsules) | |
|---|---|
| active ingredient | 1250 g |
| talc | 180 g |
| wheat starch | 120 g |
| magnesium stearate | 80 g |
| lactose | 20 g |

The pulverulent substances are forced through a sieve of 0.6 mm mesh size and mixed together. 0.33 g portions of the mixture are introduced into gelatin capsules using a capsule-filling machine.

EXAMPLE 24

10,000 tablets are prepared, each tablet comprising 5 mg of active ingredient, for example one of the compounds prepared according to Examples 1 to 22:

| Composition | |
|---|---|
| active ingredient | 50.00 g |
| lactose | 2535.00 g |
| corn starch | 125.00 g |
| polyethylene glycol 6000 | 150.00 g |
| magnesium stearate | 40.00 g |
| purified water quantum satis | |

Procedure All the pulverulent constituents are passed through a sieve of 0.6 mm mesh size. Then the active ingredient, the lactose, the magnesium stearate and half of the starch are mixed together in a suitable mixer. The other half of the starch is suspended in 65 ml of water and the resulting suspension is added to a boiling solution of the polyethylene glycol in 260 ml of water. The resulting paste is added to the powder mixture and granulated, if necessary with the addition of more water. The granules are dried overnight at 35° C., forced through a sieve of 1.2 mm mesh size and compressed to form tablets having a breaking notch.

EXAMPLE 25

4-Amidino-2-propylindanone-1-amidinohydrazone dihydrochloride

Analogously to Example 21, the title compound is prepared starting from 2-bromobenzyl bromide and malonic acid diethyl ester, m.p.>250° C.; MS(FAB): (M+H)$^+$=273; $^1$H-NMR (D$_2$O): δ=7.98 (d,1H); 7.67 (m,1H); 7.49 (t,1H); 3.44 (m,2H); 3.01 (m,1H); 1.1–1.75 (m,4H); 0.81 (t,3H).

The following Examples of acid addition salts of bases of formula I with acids [PA] also serve to illustrate the invention but do not limit the scope thereof in any way.

Temperatures are given in degrees Celsius (°C.). If no temperature is indicated, the reaction concerned is carried out at room temperature. If concentration by evaporation is carried out, a rotary, evaporator is used unless otherwise indicated.

The values for proton nuclear magnetic resonance spectroscopy are given in ppm ("parts per million") based on tetramethylsilane (δ=0) as the internal standard. d=doublet, s=singlet, t=triplet, m=multipier.

In the case of elemental analyses, the empirical formula, the molecular weight, and calculated and found analysis values are indicated.

The shortened forms and abbreviations used have the following meanings:

| | |
|---|---|
| anal. | elemental analysis |
| calc. | calculated |
| D$_2$O | dideuterium oxide |
| DMSO-d$_6$ | completely deuterised dimethyl sulfoxide |
| $^1$H-NMR | proton neclear magnetic resonance spectroscopy |
| m.p. | melting point |
| decomp. | with decomposition |

EXAMPLE 26

4-Amidino-1-indanone-2'-amidinohydrazone dicyclamate

A solution of 717 mg (4 mmol) of N-cyclohexylsulfamic acid in 20 ml of methanol is added to a solution of 460 mg (2 mmol) of 4-amidinoindanone-1-amidinohydrazone in 80 ml of methanol and the batch is concentrated to dryness by evaporation. The residue is dissolved in ethanol and crystallised by the addition of diethyl ether to yield the title compound, m.p. 210° (decomp.); $^1$H-NMR (D$_2$O): δ7.97 (d,1H); 7.64 (d,1H); 7.47 (t,1H); 3.25 (m,2H); 2.9 (m,4H); 1–2 (m,20H); anal. for C$_{23}$H$_{40}$N$_8$O$_6$S$_2$ (588.75): cacl. 46.92% C, 6.85% H, 19.03% N, found 46.5% C, 6.9% H, 19.0% N.

The starting material is prepared as follows:

a) 4-Amidino-1-indanone-2'-amidinohydrazone 9.63 g (30 mmol) of 4-amidino-1-indanone-2'-amidinohydrazone dihydrochloride (prepared in accordance with one of the processes described in Examples 1, 5, 6, 15 or 20, for example in accordance with Example 1)) are dissolved in 900 ml of distilled water heated to 70°–80° C. and cooled to 10° C. 30 ml of 2N sodium hydroxide solution are added dropwise to the resulting solution with stirring. The product which separates out is filtered off with suction, washed with a small amount of ice-water and dried to yield the title compound, m.p. 250° (decomp.).

EXAMPLE 27

4-Amidino-1-indanone-2'-amidinohydrazone dioctanoate

631 μl (4 mmol) of octanoic acid are added to a solution of 460 mg (2 mmol) of 4-amidino-1-indanone-2'-amidinohydrazone (Example 26a)) in 80 ml of methanol and the batch is concentrated to dryness by evaporation. The residue is dissolved in ethanol and crystallised by the addition of diethyl ether to yield the title compound, m.p. 190° (decomp.); $^1$H-NMR (DMSO-d$_6$): δ8.03 (d,1H); 7.52 (d,1H); 7.47 (t,1H); 3.19 (m,2H); 2.85 (m,2H); 1.98 (t,4H); 1.42 (m,4H); 1.19 (s,24H); 0.81 (t,6H); anal. for C$_{27}$H$_{46}$N$_6$O$_4$ (518.70): calc. 62.52% C, 8.94% H, 16.20% N, found 62.3% C, 8.9% H, 16.2% N.

EXAMPLE 28

4-Amidino-1-indanone-2'-amidinohydrazone disalicylate

A solution of 830 mg (6 mmol) of salicylic acid in 50 ml of ethanol is added to a solution of 690 mg (3 mmol) of 4-amidino-lindanone-2'-amidinohydrazone (Example 26a)) in 100 ml of methanol and the reaction mixture is concentrated to half the volume by evaporation. 70 ml of water are added to the solution, whereupon the title compound crystallises out, m.p. 206°–9°(decomp.); anal. for C$_{25}$H$_{26}$N$_6$O$_6$ (507.1): calc. 59.13% C, 5.19% H, 16.55% N, found 59.3% C, 5.2% H, 16.8% N.

EXAMPLE 29

4-Amidino-1-indanone-2'-amidinohydrazone dibenzenesulfonate

A solution of 975 mg (6 mmol) of benzenesulfonic acid in 50 ml of methanol is added to a solution of 690 mg (3 mmol) of 4-amidino-1-indanone-2'-amidinohydrazone (Example 26a)) in 100 ml of methanol and the batch is concentrated to dryness by evaporation. The residue is crystallised from ethanol to yield the title compound, m.p.>250° (decomp.); $^1$H-NMR (D$_2$O): δ7.38–7.95 (m,16H); 3.21 (m,2H); 2.78 (m,2H); anal. for C$_{23}$H$_{26}$N$_6$O$_6$S$_2$ (546.63): calc. 50.54% C, 4.79% H, 15.37% N, found 50.4% C, 4.8% H, 15.6% N.

EXAMPLE 30 further salts

EXAMPLE 30a

4-Amidinoindanone-1-amidinohydrazone succinate

A solution of 472 mg (4 mmol) of succinic acid in 120 ml of methanol is added to a solution of 920 mg (4 mmol) of 4-amidino-1-indanone-2'-amidinohydrazone in 120 ml of methanol. The product which crystallises out is filtered off with suction, washed with a small amount of methanol and dried to yield the title compound, m.p. 200° (decomp.); anal. for C$_{15}$H$_{20}$N$_6$O$_4$1.4 H$_2$O (367.10): calc. 49.08% C, 6.06% H, 22.89% N, found 49.13% C, 6.07% H, 23.04% N.

EXAMPLE 30b

4-Amidinoindanone-1-amidinohydrazone adipate

A solution of 146 mg (1 mmol) of adipic acid in 25 ml of ethanol is added to a solution of 230 mg (1 mmol) of 4-amidino-1-indanone-2'-amidinohydrazone in 30 ml of methanol. The product which crystallises out is filtered off with suction, washed with a small amount of ethanol and dried to yield the title compound, m.p. 200° (decomp.); anal.

for $C_{17}H_{24}N_6O_4 \cdot 0.25\ H_2O$ (380.92): calc. 53.60% C, 6.48% H, 22.06% N, found 53.79% C, 6.73% H, 21.93% N.

EXAMPLE 30c

4-Amidinoindanone-1-amidinohydrazone-1,5-naphthalene disulfonate

A solution of 1.49 g (4 mmol) of 1,5-naphthalene disulfonic acid in 100 ml of methanol is added to a solution of 920 mg (4 mmol) of 4-amidino-1-indanone-2-amidinohydrazone in 120 ml of methanol. The product which crystallises out is filtered off with suction, washed with a small amount of methanol and dried to yield the title compound, m.p.>250°; anal. for $C_{21}H_{22}N_6O_6S_2 \cdot 2.36\ H_2O$ (561.09): calc. 44.95% C, 4.80% H, 14.98% N, found 45.06% C, 4.98% H, 15.21% N.

EXAMPLE 30d

4-Amidinoindanone-1-amidinohydrazone ethane disulfonate

Analogously to any one of the Examples 26 to 30c) given hereinbefore, 4-amidino-1-indanone-2'-amidinohydrazone is converted into the title compound using 1,2-ethanedisulfonic acid.

EXAMPLE 30e

4-Amidinoindanone-1-amidinohydrazone L-tartrate

A solution of 600 mg (4 mmol) of L-(+)-tartaric acid in 100 ml of methanol is added to a solution of 920 mg (4 mmol) of 4-amidino-1-indanone-2'-amidinohydrazone in 120 ml of methanol. The product which crystallises out is filtered off with suction, washed with a small amount of methanol and dried to yield the title compound, m.p. 190° (decomp.); anal. for $C_{15}H_{20}N_6O_6 \cdot 0.26\ H_2O$ (385.04): calc. 46.79% C, 5.37% H, 21.83% N, found 46.83% C, 5.43% H, 21.87% N.

EXAMPLE 30f

4-Amidinoindanone-1-amidinohydrazone citrate

A solution of 210 mg (1 mmol) of citric acid in 10 ml of methanol is added to a solution of 230 mg (1 mmol) of 4-amidino-1-indanone-2'-amidinohydrazone in 30 ml of methanol. The product which crystallises out is filtered off with suction, washed with a small amount of methanol and dried to yield the title compound, m.p.>220° (decomp.); anal. for $C_{17}H_{22}N_6O_7$ (422.40): calc. 48.34% C, 5.25% H, 19.90% N, found 48.23% C, 5.33% H, 20.07% N.

EXAMPLE 30g

4-Amidinoindanone-1-amidinohydrazone dilactate

Analogously to any one of the Examples given hereinbefore and hereinafter, 4-amidino-1-indanone-2'-amidinohydrazone is converted into the title compound using lactic acid.

EXAMPLE 31

Analogously to any one of the above Examples 26 to 30g, the following starting compounds can be converted into the acid addition salts of octanoic acid, succinic acid, adipic acid, salicylic acid, cyclohexylsulfamic acid, ethanedisulfonic acid, benzenesulfonic acid, citric acid, tartaric acid and 1,5-naphthalenedisulfonic acid:

a) 4-amidino-1-indanone-2'-(N-hydroxyamidino)-hydrazone dihydrochloride (Example 2);
b) 5-Amidino-1-tetralone-2'-amidinohydrazone dihydrochloride (Example 3);
c) 4-Thiocarbamoyl-1-indanone-2'-amidinohydrazone hydrochloride (Example 4);
d) 4-(N-Hydroxyamidino)-1-indanone-2'-amidinohydrazone dihydrochloride (Example 7);
e) 4-Amidino-2-methyl-1-indanone-2'-amidinohydrazone dihydrochloride (Example 8);
f) 5-Amidino-6-methoxy-1-tetralone-2'-amidinohydrazone dihydrochloride (Example 9);
g) 4-Amidino-6-methoxy-7-methyl-1-indanone-2'-amidinohydrazone dihydrochloride (Example 11);
h) 4-Amidino-6,7-dimethyl-1-indanone-2'-amidinohydrazone dihydrochloride (Example 12);
i) 4-Amidino-7-hydroxy-3-methyl-1-indanone-2'-amidinohydrazone dihydrochloride (Example 13);
j) 4-(Methylamidino)-1-indanone-2'-amidinohydrazone dihydrochloride (Example 14);
k) 4-Amidino-6,7-dimethoxy-1-indanone-2'-amidinohydrazone dihydrochloride (Example 18);
l) 4-Amidino-6-methyl-1-indanone-2'-amidinohydrazone dihydrochloride (Example 10);
m) 4-Amidino-3-methyl-1-indanone-2'-amidinohydrazone dihydrochloride (Example 19);
n) 4-Amidino-2-ethyl-1-indanone-2'-amidinohydrazone dihydrochloride (Example 21);
o) 4-Amidino-2-n-butyl-1-indanone-2'-amidinohydrazone dihydrochloride (Example 22).
p) 4-Amidino-2-n-propyl-indanone-1-amidinohydrazone (Example Q).

EXAMPLE 32

Capsules, each containing 0.25 g of active ingredient, for example one of the acid addition salts of Examples 26 to 31, can be prepared as follows:

| Composition (for 5000 capsules) | |
| --- | --- |
| active ingredient | 1250 g |
| talc | 180 g |
| wheat starch | 120 g |
| magnesium stearate | 80 g |
| lactose | 20 g |

The pulverulent substances are forced through a sieve having a mesh size of 0.6 mm and mixed. 0.33 g portions of the mixture are introduced into gelatin capsules by means of a capsule-filling machine.

Example 33

10,000 tablets, each comprising 5 mg of active ingredient, for example one of the acid addition salts prepared in Examples 26 to 31, are prepared:

| Composition | |
| --- | --- |
| active ingredient | 50.00 g |
| lactose | 2535.00 g |
| corn starch | 125.00 g |
| polyethylene glycol 6000 | 150.00 g |
| magnesium stearate | 40.00 g |
| purified water quantum satis | |

Method: All of the pulverulent constituents are passed through a sieve having a mesh size of 0.6 mm. The active ingredient, the lactose, the magnesium stearate and half of the starch are then mixed in a suitable mixer. The other half of the starch is suspended in 65 ml of water and the resulting suspension is added to a boiling solution of the polyethylene glycol in 260 ml of water. The resulting paste is added to the powder mixture and granulated, where appropriate with the addition of more water. The granules are dried overnight at 35° C., forced through a sieve having a mesh size of 1.2 mm and compressed to form tablets having a breaking notch.

What is claimed is:

1. A compound of formula I

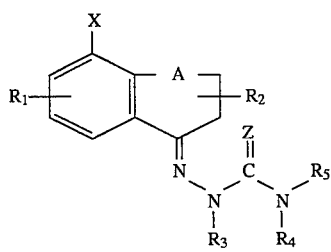

wherein A is —$(CH_2)_n$—, wherein n is 1, 2 or 3; X is a radical —C(=Y)—$NR_6R_7$; Y is $NR_8$; Z is $NR_9$; $R_1$ and $R_2$ are each independently of the other hydrogen or one or more substituents selected from the group consisting of lower alkyl, trifluoromethyl, cycloalkyl, aryl-lower alkyl, hydroxy, lower alkoxy, aryl-lower alkoxy, aryloxy, halogen, amino, N-lower alkylamino, N,N-di-lower alkylamino, lower alkanoylamino, nitro, lower alkanoyl, arylcarbonyl, mercapto, lower alkylthio, lower alkylsulfonyl, sulfamoyl, N-lower alkylsulfamoyl and N,N-di-lower alkylsulfamoyl, aryl being phenyl or naphthyl that is unsubstituted or substituted by one or more substituents from the group consisting of lower alkyl, lower alkoxy, hydroxy, nitro, amino, halogen, trifluoromethyl, lower alkanoyl, benzoyl that is unsubstituted or substituted by lower alkyl, lower alkoxy, hydroxy, halogen or by trifluoromethyl, lower alkylsulfonyl, sulfamoyl, N-lower alkylsulfamoyl and N,N-di-lower alkylsulfamoyl; the radicals $R_3$, $R_4$, $R_6$, $R_8$ and $P_9$ are each independently of the others hydrogen or lower alkyl; and $R_5$ and $R_7$ are each independently of the other hydrogen, lower alkyl, hydroxy, lower alkoxy, amino, lower alkylamino, di-lower alkyl amino, lower alkyleneamino or oxa-, thia- or aza-lower alkyleneamino; a tautomer thereof, or a pharmaceutically acceptable salt thereof.

2. A compound of formula I according to claim 1 wherein A is —$(CH_2)_n$—, wherein n is 1 or 2; X is a radical —C(=Y)—$NR_6R_7$; Y is $NR_8$; Z is $NR_9$; $R_1$ and $R_2$ are each independently of the other hydrogen or one or two substituents from the group consisting of lower alkyl, trifluoromethyl, cycloalkyl, aryl-lower alkyl, hydroxy, lower alkoxy, aryl-lower alkoxy, aryloxy, halogen, amino, N-lower alkylamino, N,N-di-lower alkylamino, lower alkanoylamino, nitro, lower alkanoyl, arylcarbonyl, mercapto, lower alkylthio, lower alkylsulfonyl, sulfamoyl, N-lower alkylsulfamoyl and N,N-di-lower alkylsulfamoyl, aryl being phenyl that is unsubstituted or substituted by lower alkyl, lower alkoxy, hydroxy, halogen, trifluoromethyl; the radicals $R_3$, $R_4$, $R_6$, $R_8$ and $R_9$ are each independently of the others hydrogen or lower alkyl; and $R_5$ and $R_7$ are each independently of the other hydrogen, lower alkyl, hydroxy, lower alkoxy, amino, lower alkylamino, di-lower alkylamino, lower alkyleneamino or oxa-, thia- or aza-tower alkylene amino; a tautomer thereof, or a pharmaceutically acceptable salt thereof.

3. A compound of formula I according to claim 1 wherein A is —$(CH_2)_n$—, wherein n is 1 or 2; X is a radical —C(=Y)—$NR_6R_7$; Y is NH; Z is NH; $R_1$ and $R_2$ are each independently of the other hydrogen or one or two substituents from the group consisting of lower alkyl, trifluoromethyl, phenyl-lower alkyl, hydroxy, lower alkoxy and halogen; the radicals $R_3$, $R_4$ and $R_6$ are hydrogen; and $R_5$ and $R_7$ are each independently of the other hydrogen, lower alkyl, hydroxy or amino; a tautomer thereof, or a pharmaceutically acceptable salt thereof.

4. A compound of formula I according to claim 1 wherein A is —$CH_2$—; X is a radical —C(=Y)—$NR_6R_7$; Y is NH; Z is NH; $R_1$ is hydrogen or one or two substituents from the group consisting of lower alkyl, hydroxy, lower alkoxy and halogen; $R_2$ is hydrogen or lower alkyl; the radicals $R_3$, $R_4$ and $R_6$ are hydrogen; and $R_5$ and $R_7$ are each independently of the other hydrogen, lower alkyl or hydroxy; a tautomer thereof, or a pharmaceutically acceptable salt thereof.

5. 5-Amidino-1-tetralone-2'-amidinohydrazone according to claim 1 or a pharmaceutically acceptable salt thereof.

6. A method for the treatment of a disorder caused by a lack of S-adenosylmethionine decarboxylase inhibition, comprising the administration of a therapeutically effective amount, inhibiting S-adenosylmethionine decarboxylase, of a compound of formula I, a tautomer thereof or a salt thereof according to claim 1 to a warm-blooded animal requiring such treatment.

* * * * *